United States Patent [19]

Levitt

[11] 4,424,073
[45] Jan. 3, 1984

[54] HERBICIDAL SULFONAMIDES

[75] Inventor: George Levitt, Wilmington, Del.

[73] Assignee: E. I. Du Pont de Nemours and Company, Wilmington, Del.

[21] Appl. No.: 370,926

[22] Filed: Apr. 22, 1982

Related U.S. Application Data

[60] Division of Ser. No. 130,343, Mar. 14, 1980, Pat. No. 4,342,587, which is a continuation-in-part of Ser. No. 59,152, Jul. 20, 1979, abandoned.

[51] Int. Cl.$^3$ .................. A01N 43/54; C07D 239/42
[52] U.S. Cl. ........................................ 71/92; 544/122; 544/123; 544/208; 544/284; 544/298; 544/312; 544/320; 544/321; 544/331; 544/332
[58] Field of Search ............... 544/122, 123, 332, 320, 544/321; 71/92

[56] References Cited

U.S. PATENT DOCUMENTS

| 3,759,921 | 9/1973 | Paget | 544/332 |
|---|---|---|---|
| 4,169,719 | 10/1979 | Levitt | 71/92 |
| 4,191,553 | 3/1980 | Reap | 544/332 |
| 4,214,890 | 7/1980 | Levitt | 71/92 |
| 4,221,585 | 9/1980 | Levitt | 71/92 |
| 4,238,621 | 12/1980 | Levitt | 544/332 |
| 4,302,241 | 11/1981 | Levitt | 544/332 |
| 4,339,266 | 7/1982 | Levitt | 71/92 |
| 4,342,587 | 8/1982 | Levitt | 71/92 |

FOREIGN PATENT DOCUMENTS 2055098 2/1981 United Kingdom ............... 544/332

Primary Examiner—Donald G. Daus
Assistant Examiner—James H. Turnipseed

[57] ABSTRACT

N-(5-substituted pyrimidin-2-ylaminocarbonyl)sulfonamides such as N-(5-chloropyrimidin-2-ylaminocarbonyl)sulfonamides are useful as herbicides.

38 Claims, No Drawings

HERBICIDAL SULFONAMIDES

This is a division, of application Ser. No. 130,343, filed Mar. 14, 1980 now U.S. Pat. No. 4,342,587 which is a continuation in part of U.S. Ser. No. 059,152 filed July 20, 1979 now abandoned.

BACKGROUND OF THE INVENTION

This invention relates to N-(5-substituted pyrimidin-2-ylaminocarbonyl)sulfonamides and their use as agricultural chemicals.

French Pat. No. 1,468,747 discloses the following para-substituted phenylsulfonamides, useful as antidiabetic agents:

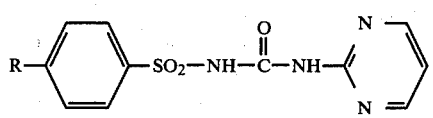

wherein $R=H$, halogen, $CF_3$ or alkyl.

Logemann et al. Chem. Ab., 53, 18052 g (1959), disclose a number of sulfonamides, including uracil derivatives and those having the formula:

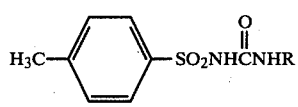

wherein R is butyl, phenyl or

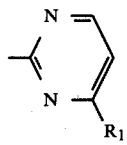

and $R_1$ is hydrogen or methyl. When tested for hypoglyemic effect in rats (oral doses of 25 mg/100 g), the compounds in which R is butyl and phenyl were most potent. The others were of low potency or inactive.

Wojciechowski, J. Acta. Polon. Pharm. 19, p. 121–5 (1962) [Chem. Ab., 59 1633 e] describes the synthesis of N-[(2,6-dimetoxypyrimidin-4-yl)aminocarbonyl]-4-methylbenzenesulfonamide:

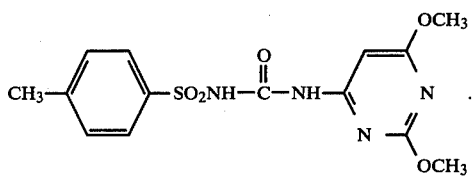

Based upon similarity to a known compound, the author predicted hypoglycemic activity for the foregoing compound.

Netherlands Patent 121,788, published Sept. 15, 1966, teaches the preparation of compounds of Formula (i), and their use as general or selective herbicides.

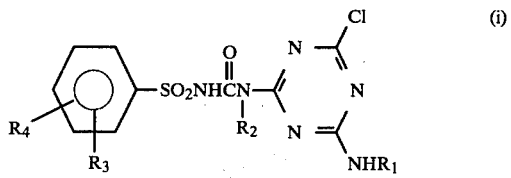

wherein $R_1$ and $R_2$ may independently be alkyl of 1–4 carbon atoms; and $R_3$ and $R_4$ may independently be hydrogen, chlorine or alkyl of 1–4 carbon atoms.

Compounds of Formula (ii), and their use as antidiabetic agents, are reported in *J. Drug. Res.* 6, 123 (1974).

wherein R is pyridyl.

The presence of undesired vegetation causes substantial damage to useful crops, especially agricultural products that satisfy man's basic food needs, such as soybeans, wheat and the like. The current population explosion and concomitant world food shortage demand improvements in the efficiency of producing these crops. Prevention or minimizing the loss of a portion of such valuable crops by killing, or inhibiting the growth of undesired vegetation is one way of improving this efficiency.

A wide variety of materials useful for killing, or inhibiting (controlling) the growth of undesired vegetation is available; such materials are commonly referred to as herbicides. The need exists, however, for still more effective herbicides that destroy or retard weeds.

SUMMARY OF THE INVENTION

According to this invention, there is provided compounds of Formula I and their agriculturally suitable salts, suitable agricultural compositions containing them, and methods of using them as selective, as well as general herbicides having both pre-emergence and post-emergence activity. These compounds are highly active herbicides. Compounds where $R_2=H$ are useful as intermediates to highly active herbicides.

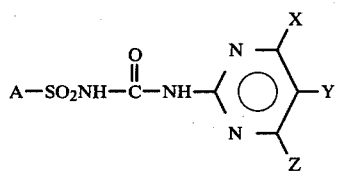

wherein

A is

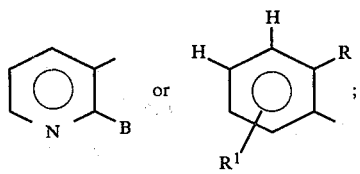

B is Cl or Br;
R is CO₂R²,

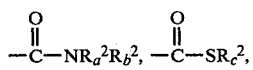

SO$_2$NR$^3$R$^4$, Cl, CF$_3$, NO$_2$ or S(O)$_n$R$^3$ where n is 0, 1 or 2;

R$^1$ is H, Cl, F, Br, NO$_2$, CH$_3$, OCH$_3$ or CF$_3$;

R$^2$ is H, C$_1$–C$_6$ alkyl, C$_3$–C$_4$ alkenyl, C$_2$–C$_3$ haloalkyl, C$_5$–C$_6$ cycloalkyl, C$_4$–C$_7$ cycloalkylalkyl, CH$_2$OCH$_2$CH$_2$OCH$_3$, CH$_2$—CH(CH$_3$)OR$^5$ or (CH$_2$)$_m$OR$^5$ where m is 1, 2 or 3;

R$_a^2$ is H, C$_1$–C$_4$ alkyl, C$_3$–C$_4$ alkenyl or OCH$_3$;

R$_b^2$ is H, C$_1$–C$_4$ alkyl, C$_3$–C$_4$ alkenyl or R$_a^2$ and R$_b^2$ can be taken together to form —CH$_2$—$_5$, —CH$_2$—$_4$ or —CH$_2$CH$_2$—O—CH$_2$CH$_2$—;

R$_c^2$ is C$_1$–C$_4$ alkyl or C$_3$–C$_4$ alkenyl;

R$^3$ is C$_1$–C$_4$ alkyl or OCH$_3$;

R$^4$ is C$_1$–C$_4$ alkyl;

R$^5$ is C$_1$–C$_3$ alkyl;

X and Z are independently H, CH$_3$, Br, Cl, OCH$_3$, CH$_2$CH$_3$, CH$_2$OCH$_3$ or OCH$_2$CH$_3$; and Y is F, Cl, Br, I, CH$_3$, CH$_2$CH$_3$, CH$_2$CH$_2$CH$_3$, (CH$_2$)$_3$CH$_3$, CH$_2$—CH=CH$_2$, OCH$_3$, OCH$_2$CH$_3$, CN, CH$_2$CH$_2$Cl, CH$_2$CH$_2$CH$_2$Cl, CH$_2$CH$_2$OCH$_3$, OCH$_2$OCH$_3$, CH$_2$OCH$_3$, OCH$_2$CH$_2$OCH$_3$, CH$_2$CO$_2$R$^6$, CH$_2$CH$_2$CO$_2$R$^6$, CO$_2$R$^6$,

or NO;

R$^6$ is CH$_3$ or CH$_2$CH$_3$; and their agriculturally suitable salts; provided that:

(1) when R$_a^2$ is OCH$_3$, then R$_b^2$ is CH$_3$;
(2) when R$^3$ is OCH$_3$, then R$^4$ is CH$_3$; and
(3) when R is Cl, then Y is F.

Preferred for reasons of higher herbicidal activity, or ease in synthesis, or both are:

(1) those compounds of Formula I, wherein R is CO$_2$R$^2$ or SO$_2$NR$_3$R$_4$.

(2) those compounds of Formula I, wherein R$^1$ is H.

More preferred for reasons of even higher herbicidal activity or more favorable ease of synthesis, or both, are:

(3) those compounds of Preferred (1) wherein R$^1$ is H.

(4) those compounds of the More Preferred (3) wherein R$^2$ is C$_1$–C$_4$ alkyl, C$_3$–C$_4$ alkenyl, or C$_2$–C$_3$ haloalkyl, and Y is F, Cl, Br, CH$_3$, C$_2$H$_5$ or CH$_2$CH$_2$Cl, and at least one of X or Z is CH$_3$, OCH$_3$, Et or OEt.

Most preferred for their yet even higher herbicidal activity or even more favorable ease of synthesis, or both are:

(5) those compounds of the More Preferred (4), wherein X is H, CH$_3$ or OCH$_3$ and Y is F, Cl, Br, CH$_3$, C$_2$H$_5$ or CH$_2$CH$_2$Cl.

Specifically preferred for highest herbicidal activity, or most favorable ease of synthesis, or both are:

Methyl 2-{[(5-chloropyrimidin-2-yl)aminocarbonyl]aminosulfonyl}benzoate;

Methyl 2-{[(4-chloro-6-methoxy-5-methylpyrimidin-2-yl)aminocarbonyl]aminosulfonyl}benzoate;

Methyl 2-[[[4-chloro-5-(2-chloroethyl)-6-methylpyrimidin-2-yl]aminocarbonyl]aminosulfonyl]benzoate;

Methyl 2-[[(4,5,6-trimethylpyrimidin-2-yl)aminocarbonyl]aminosulfonyl]benzoate;

Methyl 2-[[(5-iodo-4,6-dimethylpyrimidin-2-yl)aminocarbonyl]aminosulfonyl]benzoate;

Methyl 2-[[(5-chloro-4,6-dimethylpyrimidin-2-yl)aminocarbonyl]aminosulfonyl]benzoate;

Methyl 2-[[(5-bromo-4,6-dimethylpyrimidin-2-yl)aminocarbonyl]aminosulfonyl]benzoate;

Methyl 2-[[(5-ethyl-4,6-dimethylpyrimidin-2-yl)aminocarbonyl]aminosulfonyl]benzoate;

2-Chloro-N-[(5-fluoro-4,6-dimethoxypyrimidin-2-yl)aminocarbonyl]benzenesulfonamide;

Methyl 2-[[(5-fluoro-4,6-dimethoxypyrimidin-2-yl)aminocarbonyl]aminosulfonyl]benzoate;

(2-Propenyl) 2-[[(5-fluoro-4,6-dimethoxypyrimidin-2-yl)aminocarbonyl]aminosulfonyl]benzoate;

Methyl 2-[[(5-chloro-4-methylpyrimidin-2-yl)aminocarbonyl]aminosulfonyl]benzoate; and Methyl 2-[[(5-ethyl-4-methylpyrimidin-2-yl)aminocarbonyl]aminosulfonyl]benzoate.

DETAILED DESCRIPTION

Synthesis

As shown in Equation 1, below, the compounds of Formula I can be prepared by the reaction of an appropriate 2-aminopyrimidine of Formula II with an appropriately substituted benzenesulfonyl isocyanate of Formula III; R being equal to CO$_2$R$^2$, SO$_2$NR$^3$R$^4$, Cl, CF$_3$, NO$_2$ or S(O)$_n$R$^3$ where n=0 or 2 and R$_1$, X, Y and Z being as previously defined above.

Equation 1

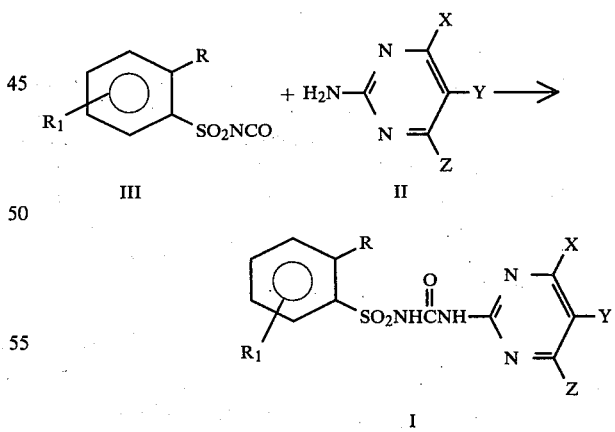

The reacton is best carried out in inert aprotic solvents such as methylene chloride, acetonitrile or tetrahydrofuran at ambient temperature. The mode of addition is not critical; however, it is often convenient to add the sulfonyl isocyanate to a stirred suspension of the aminopyrimidine since the isocyanates are usually liquids or low melting solids and their addition is more easily controlled. The reaction is generally mildly exothermic. In some cases, the desired product is soluble in the warm reaction medium and crystallizes from it in pure form on cooling. Products soluble in the reaction mixture are isolated by evaporation of the solvent, trituration of the solid residue with solvents such as 1-chlorobutane ethyl ether or pentane and filtration.

The intermediate sulfonyl isocyanates of Formula III can be prepared by reacting corresponding sulfonamides with phosgene in the presence of n-butyl isocyanate at reflux in a solvent such as chlorobenzene, according to the procedure of H. Ulrich and A. A. Y. Sayigh, *Newer Methods of Preparative Organic Chemistry*, Vol. VI p 223–241, Academic Press, New York and London, W. Foerst Ed. In cases where formation of the desired sulfonyl isocyanate is difficult by the above procedure the sulfonylurea formed by reaction of butyl isocyanate with the appropriate sulfonamide is treated with phosgene according to the above reference.

Benzenesulfonyl isocyanates with o-alkoxycarbonyl and o-sulfamoyl substituents are novel. These are prepared according to Equation 2.

Equation 2

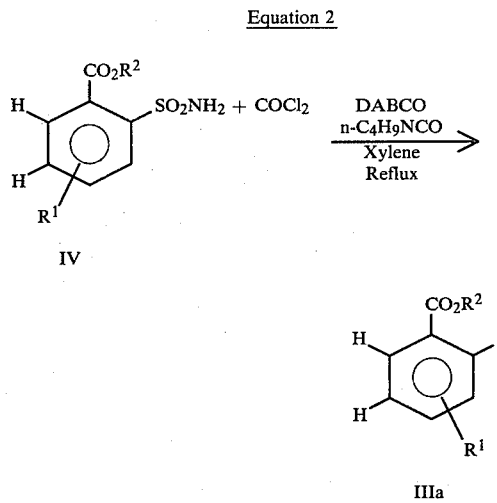

A mixture of the appropriate sulfonamide, e.g. an o-alkoxycarbonyl benzenesulfonamide IV such as the methyl ester, which is known in the art, an alkyl isocyanate such as butyl isocyanate and a catalytic amount of 1,4-diaza[2,2,2]bicyclooctane (DABCO) in xylene or other inert solvent of sufficiently high boiling point (e.g. >135°) is heated to approximately 135°. Phosgene is added to the mixture until an excess of phosgene is present as indicated by a drop in the boiling point. The mixture is heated further to drive off the excess phosgene. After the mixture is cooled and filtered to remove a small amount of insoluble by-products, the solvent and alkyl isocyanate are distilled off in-vacuo leaving a residue which is the crude sulfonyl isocyanate IIIa.

The novel pyridinesulfonyl isocyanates can also be prepared by the procedure of Equation 2 by substituting the appropriate 2-chloro or bromo pyridine sulfonamide for the o-alkoxycarbonyl benzenesulfonamide IV shown above.

The preparation of sulfonamides from ammonium hydroxide and sulfonyl chlorides is widely reported in the literature, e.g. Crossley et al., *J. Am. Chem. Soc.* 60, 2223 (1938).

Certain sulfonyl chlorides are best prepared by chlorosulfonation of a substituted benzene or thiophene according to the teaching of H. T. Clarke et al. *Org. Synth.* Coll. Vol. 1, 2nd Ed. 1941, p. 85. Other benzenesulfonyl chlorides are best made by diazotization of the appropriate aniline with sodium nitrite in HCl as taught by H. L. Yale and F. Sowinski, *J. Org. Chem.* 25, 1824 (1960).

Compounds of Formula V can be prepared by reacting appropriately substituted 2-aminopyrimidines of Formula II with 2-halo-3-pyridinesulfonyl isocyanates, Formula VI (B=Br, Cl) as shown in Equation 3.

Equation 3

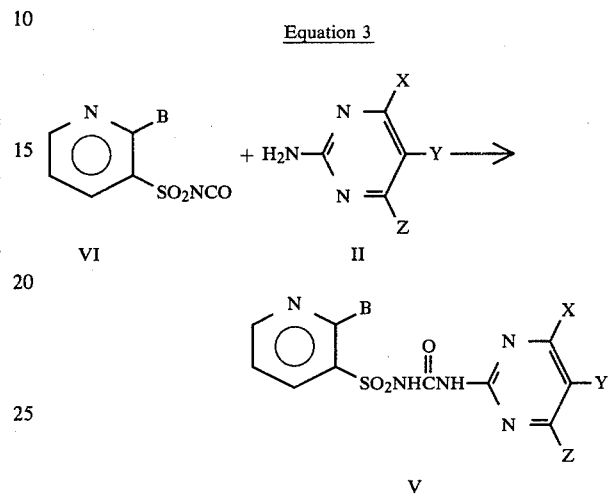

Compounds of Formula Ia, where R is equal to

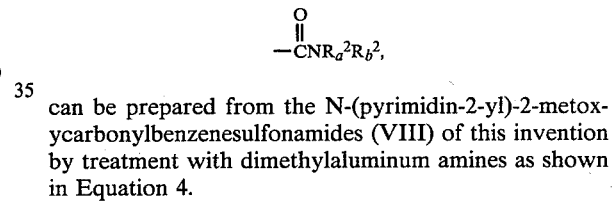

can be prepared from the N-(pyrimidin-2-yl)-2-metoxycarbonylbenzenesulfonamides (VIII) of this invention by treatment with dimethylaluminum amines as shown in Equation 4.

Equation 4

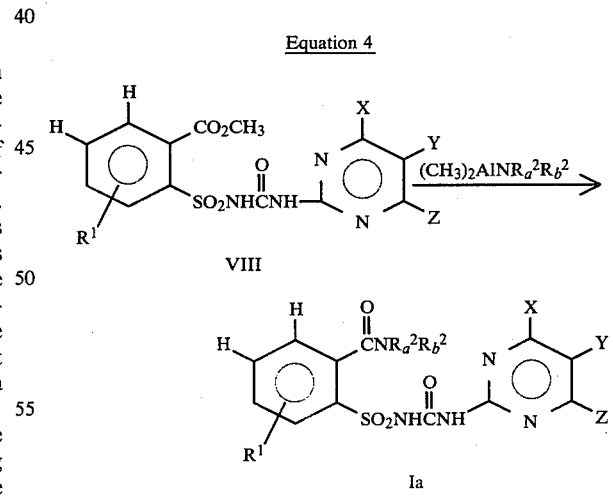

The intermediate alkylaminoaluminum compounds prepared according to A. Basha, M. Lipton and S. W. Weinreb, *Tetrahedron Letters* 4171 (1977), are mixed with a suspension of the esters in toluene or similar inert solvent and the mixture is refluxed for one to six hours. The product can be isolated by evaporation of the solvent toluene, adding methylene chloride and aqueous hydrochloric acid to decompose the residual reaction mass and extracting the desired product into methylene chloride. Evaporation of the methylene chloride yields the desired product in sufficiently pure form for the purpose of this invention.

Compounds of Formula Ib, where R is equal to

can be prepared from the N-(pyrimidin-2-yl)-2-methoxybenzenesulfonamide VIII, of this invention by treatment with dimethylaluminum alkylthiolates as shown in Equation 5.

Equation 5

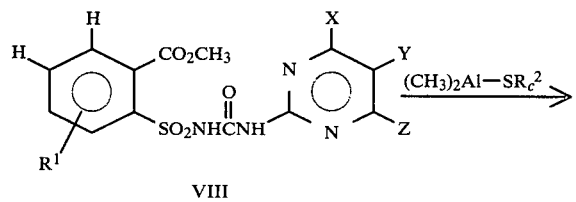

VIII

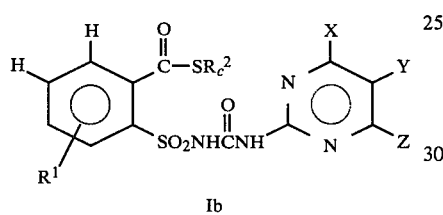

Ib

The intermediate aluminum thiolates can be prepared according to R. P. Hatch and S. W. Weinreb, *Journal of Organic Chemistry*, Vol. 42, 3960 (1977). The reaction of the thiolate with the ester of this invention is best carried out in a neutral solvent such as toluene or xylene at reflux for one to three hours. Best results are obtained when the aluminum thiolate compound is present in excess of the stoichiometric amount required.

Compounds of Formula Id, where R is equal to $SOR^3$ can be prepared from the appropriate compounds of Formula Ic where R is equal to $SR^3$; R, X, Y and Z being as previously defined, by oxidation with m-chloroperbenzoic acid according to Equation 6.

Equation 6

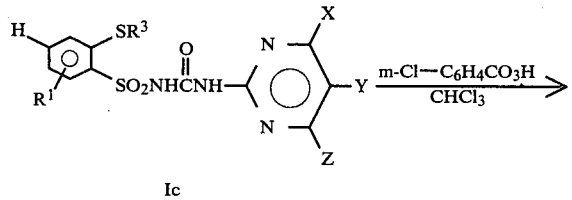

Ic

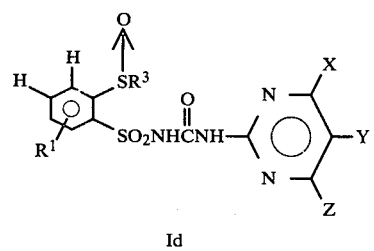

Id

The reaction can be carried out by stirring equivalent amounts of Ic with m-chloroperbenzoic acid in an inert solvent such as chloroform and stirring at 0° C. to reflux for 12–24 hours after which the insoluble m-chlorobenzoic acid produced is removed by filtration and the chloroform solution containing the desired sulfoxide is concentrated to yield the crude product. The product can be purified further by dissolving it in aqueous base of pH 10 and adjusting the pH to 4 to precipitate the desired compound while leaving the m-chlorobenzoic acid in solution as its sodium salt.

Compounds of Formula Ie, wherein $R^2$ is —H, can be prepared by hydrolysis of esters of Formula VIII wherein $R^2$ is $C_1$-$C_6$ alkyl. As shown in Equation 7, alkali metal base catalyzed hydrolysis in aqueous methanol produces the alkali metal carboxylate from which the carboxylic acid is obtained by treatment with mineral acids such as HCl:

Equation 7

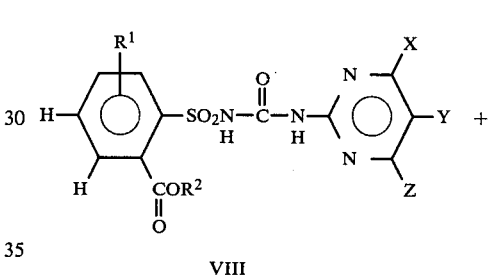

VIII

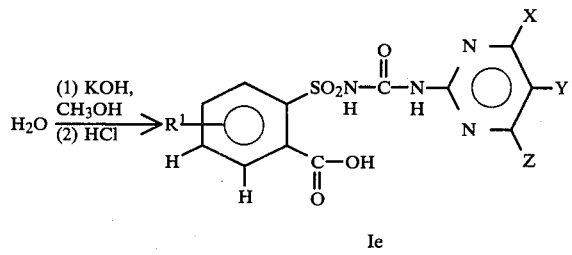

Ie

The reaction of Equation 7 is best carried out in a solution containing the compound being hydrolyzed, 2 to 10 parts of methanol, 10–50 parts of water and 2–10 equivalents of a base such as sodium or potassium hydroxide maintaining the temperature at 15°–90° C. for 3–24 hours. The reaction yields the soluble alkali metal salt of the carboxylic acid, which is suitable for the purposes of this invention. Conversion of these salts to the acid form is easily carried out by addition to the reaction medium of strong mineral acids, such as hydrochloric or sulfuric acid, causing the desired carboxylic acids to precipitate from solution.

Compounds wherein $R^2$ is H can be converted to compounds of this invention where $R^2$ is a higher alkyl or substituted hydrocarbyl group, as already disclosed herein, by the reaction of salts of the parent acid ($R^2$=H) with $R^2$-Halogen as shown in Equation 8.

Equation 8

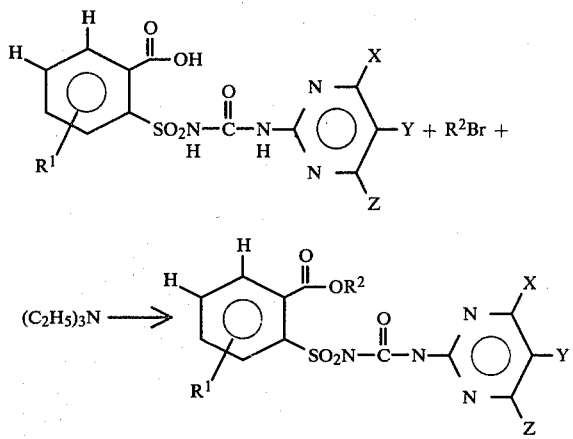

The reaction of Equation 8 is of use where the intermediate compound $R^2$-Halogen contains a readily replaceable halogen as is the case for substituted or unsubstituted allylic halides, or alkoxyalkyl halides.

The procedure of Equation 8 is best carried out in inert polar solvents such as tetrahydrofuran, acetonitrile or acetone by combining the apppropriately substituted carboxylic acid and base such as triethylamine or 1,4-diaza[2,2,2]bicyclooctane adding the appropriate halide and heating the mixture to reflux with stirring for 1 to 16 hours. The reaction mixture can be evaporated to dryness and the residue triturated with water, filtered and washed with water to separate the desired product from the water soluble salt.

Certain compounds of Formula I, where $R^2$-Halogen is less reactive, are more conveniently prepared by reaction of the silver salt of the carboxylic acid and the appropriate $R^2$-Halogen. The reaction is carried out in a suitable solvent such as acetonitrile between 0° and 80° for 1–6 hours and the product is isolated as described above.

The synthesis of heterocyclic amine derivatives has been reviewed in "The Chemistry of Heterocyclic Compound", a series published by Interscience Publ., New York and London. 2-Aminopyrimidines are described by D. J. Brown in "The Pyrimidines", Vol. XVI of the above series.

The principal synthesis of 5-substituted 2-aminopyrimidines is carried out by reacting guanidine with suitably substituted β-dicarbonyl compounds such as β-diketones, β-aldehydoketones, malonic esters, and β-ketoesters. Preparation of 5-halogen-2-aminopyrimidines with N-halogen succinimide has been taught by T. Wishiwaki, *Tetrahedron* 22, 2401 (1966).

Agriculturally suitable salts of compounds of Formula I are also useful herbicides and can be prepared in a number of ways known to the art. For example, metal salts can be made by treating compounds of Formula I with a solution of an alkali or alkaline earth metal salt having a sufficiently basic anion (e.g. hydroxide, alkoxide, carbonate or hydride). Quaternary amine salts can be made by similar techniques.

Salts of compounds of Formula I can also be prepared by exchange of one cation for another. Cationic exchange can be effected by direct treatment of an aqueous solution of a salt of a compound of Formula I (e.g. alkali or quaternary amine salt) with a solution containing the cation to be exchanged. This method is most effective when the desired salt containing the exchanged cation is insoluble in water and can be separated by filtration.

Exchange may also be effected by passing an aqueous solution of a salt of a compound of Formula I (e.g. an alkali metal or quaternary amine salt) through a column packed with a cation exchange resin containing the cation to be exchanged. In this method, the cation of the resin is exchanged for that of the original salt and the desired product is eluted from the column. This method is particularly useful when the desired salt is water-soluble.

Acid addition salts, useful in this invention, can be obtained by reacting a compound of Formula I with a suitable acid, e.g. p-toluenesulfonic acid, trichloroacetic acid or the like.

The compounds of this invention and their preparation are further illustrated by the following examples wherein temperatures are given in degrees centigrade and parts are by weight unless otherwise designated.

EXAMPLE 1

Methyl 2-(isocyanatosulfonyl)benzoate

A stirred mixture containing 157 g of methyl 2-sulfamoylbenzoate, 73 g of butyl isocyanate, 0.3 g of 1,4-diazabicyclo[2,2,2]octane and 1.0 l of xylene was heated to reflux for one half hour. Phosgene gas was then passed into the system under a dry ice reflux condenser allowing the reaction temperature to drop to 120°. This addition was continued until the reflux temperature remained at 120° without further phosgene addition. The temperature of the reaction mixture was then raised to 136° (by removal of the dry ice reflux condenser) after which it was cooled to room temperature and filtered. Evaporation of the filtrate yielded the desired crude sulfonyl isocyanate which could be purified by distillation at 132°–138° C. under 1.0 to 1.1 mm of mercury pressure. The product is extremely reactive with water so contact with moisture should be scrupulously avoided.

EXAMPLE 2

Isopropyl 2-(isocyanatosulfonyl)benzoate

To 60.7 g (0.25 mole) of isopropyl 2-sulfamoylbenzoate in 300 ml dry (molecular sieves) xylenes was added 25.0 g (0.25 mole) N-butyl isocyanate and 0.1 g 1,4-diazabicyclo[2,2,2]octane. The mixture was heated to reflux temperature and phosgene was slowly bubbled through the solution for two hours.

An infrared spectrum of the reaction mixture indicated formation of the desired sulfonyl isocyanate (2250 cm$^{-1}$). The resulting cloudy solution was cooled to room temperature and decanted from a small amount of solid impurity. Evaporation of the resulting clear solution yielded the desired crude sulfonyl isocyanate, which was used in subsequent steps without further purification.

EXAMPLE 3

Methyl 2-{[(5-chloropyrimidin-2-yl)aminocarbonyl]aminosulfonyl}benzoate

2-Amino-5-chloropyrimidine (1.3 g) was suspended in 20 ml of methylene chloride and to this was added with stirring 2.4 g of methyl 2-(isocyanatosulfonyl)benzoate. After stirring for three hours at ambient temperature, the desired product, 2-{[(5-chloropyrimidin-2-yl)aminocarbonyl]aminosulfonyl}benzoic acid, methyl ester, which had precipitated as a white solid, was filtered off. It melted at 217°-221° and showed peaks in the nuclear magnetic resonance spectrum (trifluoroacetic acid solvent) at 4.0δ(singlet) for OCH$_3$, 9.0δ for H at the 4- and 6-position of the hetero ring and at 7.9δ and 8.2-8.4δ for aromatic H, consistent for the above-named product.

EXAMPLE 4

Methyl 2-{[(4-chloro-6-methoxy-5-methylpyrimidin-2-yl)aminocarbonyl]aminosulfonyl}benzoate To 1.0 g of 2-amino-4-chloro-6-methoxy-5-methylpyrimidine in 35 ml of anhydrous acetonitrile, with stirring at ambient temperature, was added 1.5 g of methyl 2-(isocyanatosulfonyl)benzoate. The mixture was stirred for 3 hours, heated to 50° and allowed to cool. The solid precipitate thus obtained was filtered off and washed with 1-chlorobutane. It melted at 204°-205° and showed infrared absorption peaks at 1740, 1710, 1650 and 1510 cm$^{-1}$, consistent for the above-named product.

EXAMPLE 5

Methyl 2-{[(4,5,6-trimethylpyrimidin-2-yl)aminocarbonyl]aminosulfonyl}benzoate

To a mixture of 1.0 gram (0.0073 mole) of 2-amino-4,5,6-trimethylpyrimidine and 5.0 ml of dried methylene chloride stirring magnetically in a 50 ml RB single neck flask, 2.1 grams of methyl 2-(isocyanatosulfonyl)benzoate was added at room temperature and the mixture stirred at room temperature for 24 hours. Butyl chloride (4 ml) was added with constant stirring and the insoluble product filtered, washed immediately with butyl chloride and dried. (Yield 1.3 grams, m.p. 152°-161°). IR (Nujol): 5.60, 5.75 (C=O), 11.25 11.90 microns; NMR (TFA-d): δ 2.30 (s, 3H, CH$_3$), 2.65 (s, 6H, 2CH$_3$), 4.00 (s, 3H, CO$_2$CH$_3$), 7.60-8.60 (m, ArH).

EXAMPLE 6

N-[(4,5,6-trimethylpyrimidin-2-yl)aminocarbonyl]-2-dimethylaminocarbonylbenzenesulfonamide To 4.1 g of N[(4,5,6-trimethylpyrimidin-2-yl)-2-methoxycarbonylbenzenesulfonamide in 75 ml of toluene is added 37 ml of a methylene chloride and toluene solution (3:5) containing 1.25 g of dimethylaluminum dimethylamide with stirring at ambient temperature. The mixture is heated to reflux (82° C.) for two hours, cooled, 10 ml of methanol added and the solvents evaporated in vacuo. The residue is treated with a mixture of methanol, water and dilute hydrochloric acid and the precipitate is filtered off to yield the desired product.

EXAMPLE 7

N-[(5-chloro-4,6-dimethylpyrimidin-2-yl)aminocarbonyl]-2-(methylthio)carbonylbenzenesulfonamide Trimethylaluminum (6.0 ml, 2 M) is charged via syringe to 15 ml dry toluene under nitrogen atmosphere and 3.8 g N-[(5-chloro-4,6-dimethylpyrimidin-2-yl)-aminocarbonyl]-2-methoxycarbonylbenzenesulfonamide is added portionwise. After stirring at room temperature for one hour, methyl mercaptan (gas) is passed through the reaction mixture until the initial temperature rise subsided, whereupon the addition is discontinued. The reaction mixture is allowed to stir at room temperature for 1 hour, and quenched with 25 ml of 10% HCl. The resultant white suspension is filtered to give the desired product.

EXAMPLE 8

N,N-Diethyl-1,2-benzenedisulfonamide

To a solution of 114 g of o-amino-N,N-diethylbenzenesulfonamide in a mixture of 400 ml of concentrated hydrochloric acid and 100 ml of glacial acetic acid was added a solution of 50 g of sodium nitrite in 130 ml of water at −5° to 0°. The solution was stirred at 0° for 15 minutes then poured into a mixture of 14 g of cuprous chloride and 100 ml of liquid sulfur dioxide in 550 ml of glacial acetic acid at 0°-5°. This mixture was stirred at 0° for 15 minutes then at room temperature for 3 hours before pouring into three liters of ice water. The crude sulfonyl chloride was filtered off and washed with water. It was then dissolved in 1 l of ethyl ether, washed with water and dried over magnesium sulfate. To this ether solution was added 20 ml of liquid anhydrous ammonia at 5°-15°. After stirring overnight at room temperature the solid was filtered off, washed with water, ethanol and then 1-chlorobutane. Oven drying at 60° gave 91.8 g N,N-diethyl-1,2-benzenedisulfonamide, m.p. 156°-9°.

NMR(DMSO-d$_6$) δ:0.9-1.2 [t, 6.0H, (CH$_3$CH$_2$)$_2$N-]; 3.2-3.6 [qt, 3.8H, (CH$_3$CH$_2$)$_2$N-]; ~7.2 (broad singlet 2.1H, NH$_2$); 7.7-8.4 (m, 4.1H, 4 aromatics).

EXAMPLE 9 o-N,N-Diethylsulfamoylbenzenesulfonyl isocyanate

A solution of 13.2 g of N,N,diethyl-1,2-benzenedisulfonamide, 4.5 g of n-butylisocyanate, and 0.2 g of 1,4-diaza[2,2,2]bicyclooctane (DABCO) in 90 ml of mixed xylenes was heated to 135°. To this solution was added 3.3 ml of liquid phosgene at such a rate that the temperature was maintained between 125° and 135° (about 2 hours). The temperature was kept at 130° for ½ hour after the addition. The solution was cooled and filtered to remove a small amount of insoluble solid then concentrated at 60°-70° in-vacuo. The residue of o-N,N-diethylsulfamoylbenzenesulfonyl isocyanate was an oil weighing 16.8 g and was sufficiently pure for further reaction.

EXAMPLE 10

N,N-Diethyl-N'-[(4,5,6-trimethylpyrimidin-2-yl)aminocarbonyl]-1,2-benzenedisulfonamide A mixture of 0.8 g of 2-amino-4,5,6-trimethylpyrimidine, 2.8 g of the crude sulfonyl isocyanate from Example 9 and a few crystals of DABCO in 25 ml of acetonitrile is stirred at room temperature for 16 hours. A small amount of unreacted aminopyrimidine is filtered off and the filtrate concentrated in-vacuo to give a hard glass. Crystallization from methanol gives N,N-diethyl-N'[4,5,6-trimethylpyrimidin-2-yl]aminocarbonyl-1,2-benzenedisulfonamide as a white solid.

EXAMPLE 11

2-Chloro-3-pyridinesulfonylisocyanate

To 125 ml of dry xylene was added with stirring 20.7 g of 2-chloro-N-(butylcarbamoyl)-3-pyridinesulfonamide. This solution was heated to reflux, and phosgene added until no further uptake of this gas was observed.

It was then cooled, filtered and the solvent removed in vacuo to yield 2-chloro-3-pyridinesulfonylisocyanate as an oil Bp 108°–110° (0.7 mm Hg) and showing a sharp absorption peak in the infrared region at 2220 cm$^{-1}$.

EXAMPLE 12

2-Chloro-N-[5-chloro-4,6-dimethylpyrimidin-2-yl)aminocarbonyl]-3-pyridinesulfonamide To a stirred suspension of 1.4 g of 2-amino-5-chloro-5,6-dimethylpyrimidine in 20 ml of dry acetonitrile at room temperature is added 2.2 g of 2-chloropyridine-3-sulfonylisocyanate. The mixture is stirred for several hours, evaporated to dryness and the residue is mixed with 30 ml of water and enough 10% sodium hydroxide to adjust the pH to 11. This mixture is filtered asnd the filtrate adjusted to pH 7 by the addition of 10% hydrochloric acid and then refiltered. Acidification of this filtrate to pH 2 causes the desired compound to precipitate. The desired compound is filtered off and dried.

By using the procedures of Examples 3–7, 10 and 12, with equivalent amounts of the appropriate aminopyrimidine and the appropriately substituted sulfonyl isocyanate, the compounds in Tables I and II can be prepared.

Alternatively, the methods of Examples 3–6 are used to obtain compounds where R is equal to $SOR^3$,

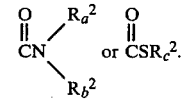

TABLE I

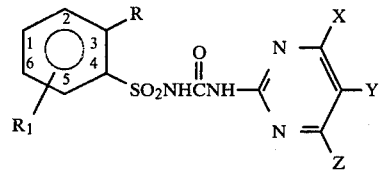

| R | R₁ | X | Y | Z | m.p. (°C.) |
|---|---|---|---|---|---|
| CO₂CH₃ | H | H | Br | H | 200–204° |
| CO₂CH₃ | H | CH₃ | Br | CH₃ | 152–155° |
| CO₂CH₃ | H | OCH₃ | Br | OCH₃ | 190–195° |
| CO₂CH₃ | H | CH₃ | CH₃ | CH₃ | 158–161° |
| CO₂CH₃ | H | CH₃ | Br | OCH₃ | 180–183° |
| CO₂CH₃ | H | OCH₃ | Cl | CH₃ | 165–170° |
| CO₂CH₃ | H | CH₃ | Cl | CH₃ | 170–174° |
| CO₂CH₃ | H | OCH₃ | Cl | OCH₃ | 186–190° |
| CO₂CH₃ | H | Cl | Cl | CH₃ | 172–174° |
| CO₂CH₃ | H | OCH₃ | CH₃ | CH₃ | 197–198° |
| CO₂CH₃ | H | H | CH₃ | OCH₃ | 185–193° |
| CO₂CH₃ | H | Cl | CH₂CH₂Cl | CH₃ | 193–196° |
| CO₂CH₃ | H | OCH₃ | CH₃ | OCH₃ | 218–219° |
| CO₂CH₃ | H | Cl | C₂H₅ | OCH₃ | 157–158° |
| CO₂CH₃ | H | CH₃ | C₂H₅ | CH₃ | 126–129° |
| CO₂CH₃ | H | Cl | C₂H₅ | CH₃ | 188–189° |
| CO₂CH₃ | H | Cl | CH₃ | CH₃ | 186–189° |
| CO₂CH₃ | H | H | Br | CH₃ | 202–203° |
| CO₂CH₃ | H | Cl | Br | Cl | 201–202° |
| CO₂CH₃ | H | H | Cl | CH₃ | 199–202° |
| CO₂CH₃ | H | Cl | Cl | Cl | 209–211° |
| CO₂CH₃ | H | OCH₃ | CH₂CH₂OCH₃ | CH₃ | 135–140° |
| CO₂CH₂OC₂H₅ | H | CH₃ | CH₃ | CH₃ | |
| CO₂CH₂OCH₃ | H | CH₃ | CH₃ | CH₃ | |
| CO₂CH₂OCH(CH₃)₂ | H | CH₃ | CH₃ | CH₃ | |
| CO₂CH₂OCH₂CH₂OCH₃ | H | CH₃ | CH₃ | CH₃ | |
| CO₂CH₃ | H | Cl | CH₂CH₂CH₂Cl | Cl | 187–189° |
| CO₂CH₃ | H | CH₃ | CH₂CH₃ | H | 168–170° |
| CO₂CH(CH₃)₂ | H | CH₃ | CH₃ | CH₃ | 200–202° |
| CO₂CH(CH₃)₂ | H | CH₃ | Cl | CH₃ | 218–220° |
| CO₂CH₂CH=CH₂ | H | CH₃ | Cl | CH₃ | 181–183° |
| CO₂CH₂CH=CH₂ | H | CH₃ | CH₃ | CH₃ | 112–114° |
| CO₂CH₃ | H | CH₃ | I | CH₃ | 198–201° |
| CO₂CH₃ | H | Cl | CH₂CH=CH₂ | Cl | 142–145° |
| CO₂CH(CH₃)₂ | H | H | Br | CH₃ | 164–170° |
| CO₂CH(CH₃)₂ | H | CH₃ | I | CH₃ | 177–182° |
| NO₂ | H | CH₃ | Cl | CH₃ | 180–190° |
| NO₂ | H | H | Cl | CH₃ | 232–237° |
| NO₂ | H | CH₃ | CH₃ | CH₃ | 190–200° |
| CO₂CH₃ | H | CH₃ | CH₂CH=CH₂ | CH₃ | 143–149° |
| CO₂CH₃ | H | CH₃ | n-butyl | CH₃ | 170–175° |
| CO₂CH₃ | H | CH₃ | CH₃ | C₂H₅ | 175–183° |
| CO₂CH₃ | H | CH₃ | n-propyl | CH₃ | 155–160° |
| CO₂CH₃ | H | CH₃ | O‖CH₂COC₂H₅ | CH₃ | 158–160° |
| CO₂CH₃ | H | CH₃ | n-butyl | OCH₃ | 188–190° |
| CO₂CH₃ | H | Cl | CH₂CH₂CH₂Cl | Cl | 187–189° |
| CO₂CH₃ | H | OC₂H₅ | Cl | CH₃ | 171–173° |

TABLE I-continued

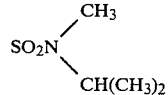

| R | R₁ | X | Y | Z | m.p. (°C.) |
|---|---|---|---|---|---|
| CO$_2$C$_2$H$_5$ | H | Cl | CH$_3$ | OCH$_3$ | |
| CO$_2$CHCH$_3$<br>    \|<br>    CH$_2$CH$_3$ | H | OCH$_3$ | F | OCH$_3$ | |
| CO$_2$CH$_2$CH=CHCH$_3$ | H | CH$_3$ | Cl | H | |
| CO$_2$CH$_2$—cyclo-C$_3$H$_5$ | H | Br | OCH$_3$ | OCH$_3$ | |
| CO$_2$CH$_2$—cyclo-C$_6$H$_{11}$ | H | OCH$_3$ | CH$_3$ | OCH$_3$ | |
| CO$_2$—cyclo-C$_6$H$_{11}$ | H | CH$_3$ | OCH$_3$ | CH$_3$ | |
| CO$_2$CH$_2$CH$_2$OCH$_3$ | H | CH$_3$ | Cl | CH$_3$ | |
| CO$_2$CH$_2$CH$_2$OCH(CH$_3$)$_2$ | H | CH$_3$ | CH$_3$ | CH$_3$ | |
| CO$_2$CH$_2$CH(CH$_3$)O—n-C$_3$H$_7$ | H | H | Cl | CH$_3$ | |
| CF$_3$ | H | CH$_3$ | CH$_2$CH$_2$Cl | Cl | |
| NO$_2$ | H | OCH$_3$ | Br | OCH$_3$ | |
| SO$_2$CH$_3$ | H | CH$_3$ | CH$_3$ | CH$_3$ | |
| SO$_2$CH(CH$_3$)$_2$ | H | CH$_3$ | Cl | CH$_3$ | |
| SO$_2$—n-C$_4$H$_9$ | H | CH$_3$ | OCH$_3$ | CH$_3$ | |
| CO$_2$CH$_3$ | H | Cl | CH$_2$CH$_2$Cl | Cl | 196–201° |
| CO$_2$CH$_3$ | H | Cl | CH$_2$CH$_2$Cl | OCH$_3$ | 167–171° |
| SO$_2$N(CH$_3$)$_2$ | H | H | CH$_3$ | OCH$_3$ | |
| SO$_2$N(CH$_3$)(CH(CH$_3$)$_2$) | H | H | Cl | CH$_3$ | |
| SO$_2$N(n-C$_4$H$_9$)$_2$ | H | CH$_3$ | I | CH$_3$ | |
| CO$_2$CH$_3$ | 5-Cl | H | Cl | H | |
| CO$_2$C$_2$H$_5$ | 5-F | CH$_3$ | I | CH$_3$ | |
| CO$_2$CH$_3$ | 5-Br | H | OCH$_3$ | CH$_3$ | |
| CO$_2$CH$_3$ | 5-NO$_2$ | H | Cl | H | |
| CO$_2$CH$_3$ | 5-CH$_3$ | H | Cl | H | |
| CO$_2$CH$_3$ | 5-OCH$_3$ | H | Cl | H | |
| CO$_2$CH$_3$ | 5-CF$_3$ | CH$_3$ | NO$_2$ | CH$_3$ | |
| —C(O)SCH$_3$ | H | CH$_3$ | NO | OCH$_3$ | |
| CO$_2$CH$_3$ | H | OCH$_3$ | F | OCH$_3$ | >300° |
| CO$_2$CH$_2$CH=CH$_2$ | H | OCH$_3$ | F | OCH$_3$ | >300° |
| CO$_2$-cyclopentyl | H | H | Cl | CH$_3$ | |
| CO$_2$CH$_2$CHClCH$_3$ | H | CH$_3$ | CH$_3$ | CH$_3$ | |
| CO$_2$CH$_3$ | H | CH$_3$ | CN | CH$_3$ | |
| CO$_2$CH$_2$CH=CH$_2$ | 5-Cl | OCH$_3$ | CH$_2$OCH$_3$ | OCH$_3$ | |
| CO$_2$CH$_2$CH=CH$_2$ | 5-NO$_2$ | OCH$_3$ | OCH$_2$CH$_2$OCH$_3$ | OCH$_3$ | |
| CO$_2$CH(CH$_3$)$_2$ | H | Br | CH$_3$ | OCH$_3$ | |
| CO$_2$CH$_3$ | H | C$_2$H$_5$ | CH$_3$ | CH$_3$ | |
| CO$_2$CH(CH$_3$)CH=CH$_2$ | H | OCH$_3$ | OCH$_2$OCH$_3$ | OCH$_3$ | |
| CO$_2$CH$_2$CHBrCH$_2$Br | H | OC$_2$H$_5$ | Cl | CH$_3$ | |
| SO$_2$N(C$_2$H$_5$)$_2$ | H | OCH$_3$ | F | OCH$_3$ | |
| SO$_2$N(CH$_3$)(CHC$_2$H$_5$)<br>          \|<br>          CH$_3$ | 5-Br | OCH$_3$ | Cl | OCH$_3$ | |
| NO$_2$ | H | CH$_3$ | CH$_2$CO$_2$C$_2$H$_5$ | CH$_3$ | |
| NO$_2$ | H | CH$_3$ | NO | CH$_3$ | |
| CF$_3$ | H | H | Cl | H | |
| SO$_2$CH(CH$_3$)$_2$ | H | OCH$_3$ | F | OCH$_3$ | |
| SO$_2$CH$_3$ | H | CH$_3$ | Cl | CH$_3$ | |
| SO$_2$C$_2$H$_5$ | 5-Cl | OCH$_3$ | F | OCH$_3$ | |
| CO$_2$CH$_2$CH$_2$CH$_2$OCH$_3$ | H | H | Cl | CH$_3$ | |
| SO$_2$N(CH$_3$)$_2$ | H | CH$_3$ | CH$_3$ | CH$_3$ | |

TABLE I-continued $$\text{Ar-SO}_2\text{NHCNH} \underset{N}{\overset{O}{\|}} \text{-pyrimidine(X,Y,Z)}$$

where Ar is phenyl substituted with R (position 3) and $R_1$ (position 5), and the pyrimidine bears X, Y, Z.

| R | $R_1$ | X | Y | Z | m.p. (°C.) |
|---|---|---|---|---|---|
| $CO_2CH_3$ | 5-$NO_2$ | $OCH_3$ | Cl | $OCH_3$ | |
| $CO_2(CH_2)_5CH_3$ | H | H | F | H | |
| $CO_2CH_3$ | H | $CH_3$ | $CH_3$ | $CH_3$ | |
| $CH(CH_3)_2$ | H | $CH_3$ | $CH_2CH_2Cl$ | Cl | |
| $NO_2$ | H | $CH_3$ | I | $CH_3$ | |
| $NO_2$ | H | $OCH_3$ | $CH_2CH=CH_2$ | Cl | |
| $CO_2C_2H_5$ | H | $CH_3$ | Cl | $CH_3$ | |
| $CO_2CH_3$ | H | H | Cl | H | |
| $CO_2$—n-$C_4H_9$ | H | $CH_3$ | Cl | $OCH_3$ | |
| $CO_2CH_2CH_2Cl$ | H | $CH_3$ | Br | $OCH_3$ | |
| $CO_2CH_2CF_3$ | H | $CH_3$ | $CO_2CH_3$ | $CH_3$ | |
| Cl | H | $OCH_3$ | F | $OCH_3$ | 216–219° |
| $-\overset{O}{\underset{\|}{C}}-SCH_2CH_3$ | H | $CH_3$ | $OCH_2CH_2OCH_3$ | H | |
| $-\overset{O}{\underset{\|}{C}}-SCH(CH_3)CH=CH_2$ | H | $OCH_3$ | CHO | $OCH_3$ | |
| $-\overset{O}{\underset{\|}{C}}-\overset{H}{N}-C_2H_5$ | H | $OCH_3$ | $OCH_3$ | $OCH_3$ | |
| $-\overset{O}{\underset{\|}{C}}-N(CH_3)_2$ | 5-Cl | $CH_3$ | $OCH_2CH_3$ | $CH_3$ | |
| $-\overset{O}{\underset{\|}{C}}-N(n-C_4H_9)_2$ | H | $CH_3$ | $CH_2OCH_3$ | $OCH_3$ | |
| $-\overset{O}{\underset{\|}{C}}-NCH_2CH_2CH=CH_2$ (NH) | 5-$NO_2$ | H | Cl | $CH_3$ | |
| $-\overset{O}{\underset{\|}{C}}-N\underset{\diagdown}{\diagup}\text{morpholino}$ | H | Cl | $CH_2CH_2Cl$ | $OCH_3$ | |
| $-\overset{O}{\underset{\|}{C}}\text{NCH(CH}_3\text{)CH=CH}_2$ (NH) | H | Cl | $CH_2CH=CH_2$ | $OCH_3$ | |
| $-\overset{O}{\underset{\|}{C}}\text{N}(CH_3)(CH(CH_3)_2)$ | H | H | Cl | $CH_3$ | |
| $-\overset{O}{\underset{\|}{C}}\text{N}(OCH_3)(C_2H_5)$ | 5-Br | Br | $(CH_2)_2CH_3$ | $CH_3$ | |
| $-\overset{O}{\underset{\|}{C}}-N\text{(pyrrolidino)}$ | 5-$CF_3$ | Cl | $OCH_2OC_2H_5$ | $OCH_3$ | |
| $-\overset{O}{\underset{\|}{C}}SCH_2CH=CH_2$ | H | $CH_3$ | $CH_3$ | $CH_3$ | |

TABLE I-continued

| R | R₁ | X | Y | Z | m.p. (°C.) |
|---|---|---|---|---|---|
| —C(=O)N(piperidine) | H | OCH₃ | F | OCH₃ | |
| —C(=O)N(pyrrolidine) | 5-OCH₃ | Cl | OCH₂CH₃ | OCH₃ | |
| —SO₂N(CH₃)(OCH₃) | F | OCH₃ | CH₂CH₂OCH₃ | Cl | |
| —SCH₃ | 5-OCH₃ | OCH₃ | CHO | OCH₃ | |
| —SOCH₃ | 5-NO₂ | CH₃ | CH₂CH₂C(=O)OCH₃ | CH₃ | |
| CO₂CH₂CH(CH₃)OCH₃ | H | CH₃ | Br | CH₃ | |
| CO₂H | H | CH₃ | CH₃ | CH₃ | |
| CO₂H | H | CH₃ | CH₃ | OCH₃ | |
| CO₂H | H | H | Cl | CH₃ | |
| C(=O)—SCH₃ | H | CH₃ | CH₃ | CH₃ | |
| NO₂ | 6-Cl | CH₃ | CH₃ | CH₃ | |
| Cl | 6-Cl | OCH₃ | F | OCH₃ | |
| NO₂ | 6-CH₃ | CH₃ | CH₃ | CH₃ | |
| —SOC₂H₅ | H | CH₃ | CH₃ | CH₃ | |
| —SO—n-C₃H₄ | H | CH₃ | Cl | CH₃ | |
| —SO—n-C₄H₉ | H | OCH₃ | Cl | CH₃ | |
| NO₂ | H | CH₃ | Cl | CH₂OCH₃ | |
| CO₂CH₃ | H | CH₃ | Cl | CH₂OCH₃ | |
| SO₂CH₃ | H | CH₃ | Cl | CH₂OCH₃ | |
| SO₂N(CH₃)₂ | H | CH₃ | Cl | CH₂OCH₃ | |
| CO₂CH(CH₃)₂ | H | CH₂OCH₃ | Cl | CH₂OCH₃ | |

TABLE II

| B | X | Y | Z | m.p. (°C.) |
|---|---|---|---|---|
| Cl | H | Cl | H | 204–211° |
| Cl | CH₃ | Br | CH₃ | |
| Cl | CH₃ | Br | OCH₃ | |
| Br | CH₃ | Cl | CH₃ | |
| Cl | CH₃ | CH₃ | CH₃ | |
| Cl | CH₃ | Cl | CH₃ | |
| Br | CH₃ | CH₃ | CH₃ | |
| Cl | CH₃ | Cl | OCH₃ | |
| Cl | H | Cl | CH₃ | |
| Br | H | Br | CH₃ | |
| Cl | OCH₃ | CH₃ | CH₃ | |
| Cl | Cl | Cl | CH₃ | |
| Cl | Cl | CH₂CH₂Cl | CH₃ | |
| Cl | Cl | CH₂CH=CH₂ | Cl | |
| Br | Cl | CH₂CH=CH₂ | OCH₃ | |
| Cl | CH₃ | CH₃ | C₂H₅ | |
| Cl | Cl | Br | Cl | |
| Br | CH₃ | CH₂CH=CH₂ | Cl | |
| Cl | OCH₃ | CH₂CH=CH₂ | Cl | |
| Cl | OCH₃ | F | OCH₃ | |
| Br | CH₃ | I | CH₃ | |
| Cl | CH₃ | I | CH₃ | |
| Cl | CH₃ | CN | CH₃ | |
| Cl | OCH₃ | CH₂CH₂Cl | Cl | |
| Cl | CH₃ | NO | CH₃ | |

Formulations

Useful formulations of the compounds of Formula I can be prepared in conventional ways. They include dusts, granules, pellets, suspensions, emulsions, wettable powders, emulsifiable concentrates and the like. Many of them can be applied directly. Sprayable formulations can be extended in suitable media and used at spray volumes of from a few liters to several hundred liters per hectare. High strength compositions are used primarily as concentrates which are to be diluted prior to ultimate use. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the approximate proportions set forth in Table 2.

TABLE 2

| | Weight Percent* | | |
|---|---|---|---|
| | Active Ingredient | Diluent(s) | Surfactant(s) |
| Wettable Powders | 20–90 | 0–74 | 1–10 |
| Oil Suspensions, Solutions Emulsions (including Emusifiable Concentrates) | 5–50 | 40–95 | 0–15 |
| Aqueous Suspensions | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active Ingredient plus at least one of a Surfactant or a Diluent equals 100 weight percent.

Lower or higher levels of active ingredient can be present, depending on the intended use and the physical properties of the compound. Higher ratios of surfactant to active ingredient are sometimes desirable, and are achieved by incorporation into the formulation, or by tank mixing.

Some typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide", 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending, and usually grinding, as in a hammer or fluid energy mill. Suspensions are prepared by wet milling (see, for example, Littler, U.S. Pat. No. 3,060,084). Granules and pellets can be made by spraying the active material on preformed granular carriers or by agglomeration techniques. See J. E. Browning, "Agglomeration", *Chemical Engineering*, Dec. 4, 1967, pp. 147ff. and "Perry's Chemical Engineer's Handbook", 4th Ed., McGraw-Hill, New York, 1963, pp. 8–59ff.

For further information regarding the art of formulation, see for example:

H. M. Loux, U.S. Pat. No. 3,235,361, Col. 6, line 16 through Col. 7, line 19 and Examples 10 through 41.

R. W. Luckenbaugh, U.S. Pat. No. 3,309,192, Col. 5, line 43 through Col. 7, line 62 and Examples 8, 12, 15, 39, 41, 52, 53, 58, 132, 138–140, 162–164, 166, 167, 169–182.

H. Gysin and E. Knusli, U.S. Pat. No. 2,891,855, Col. 3, line 66 through Col. 5, line 17 and Examples 1–4.

G. C. Klingman, "Weed Control as a Science", John Wiley & Sons, Inc., New York, 1961, pp. 81–96.

J. D. Fryer and S. A. Evans, "Weed Control Handbook", 5th Ed., Blackwell Scientific Publications, Oxford, 1968, pp. 101–103.

Unless indicated otherwise, all parts are by weight in the following examples.

EXAMPLE 13

High Strength Concentrate

Methyl 2-{[(5-chloropyrimidin-2-yl)aminocarbonyl]aminosulfonyl}benzoate—98.5%
silica aerogel—0.5%
synthetic amorphous fine silica—1.0%

The ingredients are blended and ground in a hammer mill to produce a high strength concentrate essentially all passing a U.S.S. No. 50 sieve (0.3 mm openings). This material may then be formulated in a variety of ways known to those skilled in the art.

EXAMPLE 14

Oil Suspension

Methyl 2-{[(4-chloro-6-methoxy-5-methylpyrimidin-2-yl)aminocarbonyl]aminosulfonyl}benzoate—25%
polyoxyethylene sorbitol hexaoleate—5%
highly aliphatic hydrocarbon oil—70%

The ingredients are ground together in a sand mill until the solid particles have been reduced to under about 5 microns. The resulting suspension may be applied directly, but preferably after being extended with oils or emulsified in water.

EXAMPLE 15

Wettable Powder

Methyl 2-{[(4-chloro-6-methoxy-5-methylpyrimidin-2-yl)aminocarbonyl]aminosulfonyl}benzoate—40%
dioctyl sodium sulfosuccinate—1.5%
sodium ligninsulfonate—3%
low viscosity methyl cellulose—1.5%
attapulgite—54%

The ingredients are thoroughly blended, passed through an air mill, to produce an average particle size under 15 microns, reblended, and sifted through a U.S.S. No. 50 sieve (0.3 mm opening) before packaging.

All compounds of the invention may be formulated in the same manner.

EXAMPLE 16

Wettable Powder

Methyl 2-{[(5-chloropyrimidin-2-yl)aminocarbonyl]aminosulfonyl}benzoate—80%
sodium alkylnaphthalenesulfonate—2%
sodium ligninsulfonate—2%
synthetic amorphous silica—3% kaolinite—13%

The ingredients are blended and coarsely ground in a hammer mill to produce particles essentially all below 100 microns in size. The material is then reblended, sifted through a U.S.S. No. 50 sieve (0.3 mm opening) and packaged.

EXAMPLE 17

Wettable Powder

Methyl 2-{[(4-chloro-6-methoxy-5-methylpyrimidin-2-yl)aminocarbonyl]aminosulfonyl}benzoate—65%
    dodecylphenol polyethylene glycol ether—2%
    sodium ligninsulfonate—4%
    sodium silicoaluminate—6%
    montmorillonite (calcined)—23%

The ingredients are thoroughly blended. The liquid surfactant is added by spraying upon the solid ingredients in the blender. After grinding in a hammer mill to produce particles essentially all below 100 microns, the material is reblended, sifted through a U.S.S. No. 50 sieve (0.3 mm opening) and packaged.

EXAMPLE 18

Wettable Powder

Methyl 2-{[(5-chloropyrimidin-2-yl)aminocarbonyl]aminosulfonyl}benzoate—50%
    sodium alkylnaphthalenesulfonate—2%
    low viscosity methyl cellulose—2%
    diatomaceous earth—46%

The ingredients are blended, coarsely hammer milled and then air milled to produce particles of active essentially all below 10 microns in diameter. The product is reblended before packaging.

EXAMPLE 19

Granule wettable powder of Example 18—10%
    attapulgite granules—90%
    (U.S.S. #20–40; 0.84–0.42 mm)

A slurry of wettable powder containing 50% solids is sprayed on the surface of attapulgite granules in a double-cone blender. The granules are dried and packaged.

EXAMPLE 20

Extruded Pellet

Methyl 2-{[(4-chloro-6-methoxy-5-methylpyrimidin-2-yl)aminocarbonyl]aminosulfonyl}benzoate—25%
    anhydrous sodium sulfate—10%
    crude calcium ligninsulfonate—5%
    sodium alkylnaphthalenesulfonate—1%
    calcium/magnesium bentonite—59%

The ingredients are blended, hammer milled and then moistened with about 12% water. The mixture is extruded as cyclinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

Utility

The compounds of the present invention are effective herbicides. They have utility for broad-spectrum pre- and/or post-emergence weed control in areas where complete control of all vegetation is desired, such as around fuel storage tanks, ammunition depots, industrial storage areas, parking lots, drive-in theaters, around billboards, highway and railroad structures. Alternatively, the subject compounds are useful for selective pre- or post-emergence weed control in crops such as wheat and barley. Certain of the subject compounds control nutsedge (Cyperus spp.) and some compounds may be used for selective weed control in soybeans. The compounds of this invention also possess plant growth regulant activity.

The rates of application for the compounds of the invention are determined by a number of factors, including their use as selective or general herbicides, the crop species involved, the types of weeds to be controlled, weather and climate, formulations selected, mode of application, amount of foliage present, etc. In general terms, the subject compounds should be applied at levels of around 0.125 to 10 kg/ha, the lower rates being suggested for use on lighter soils and/or those having a low organic matter content, for selective weed control or for situations where only short-term persistence is required.

Combinations of the compounds of Formula I with known herbicides provide effective control of weeds in small grain crops such as wheat and barley. Typical herbicides that may be used are chlorotoluron-[3-(3-chloro-4-methylphenyl)-1,1-dimethylurea], MCPP [(±)-2-(4-chloro-2-methylphenoxy)propanoic acid], metoxuron [3-(3-chloro-4-methoxyphenyl)-1,1-dimethylurea], methabenzthiazuron [1-(benzothiazol-2-yl)-1,3-dimethylurea], dichlofop [(methyl-2-[4-(2,4-dichlorophenoxy)phenoxy]propanoate)], tri-allate[S-2,3-dichloroallyl di-isopropylthiocarbamate], isoproturon[3-(4-isopropylphenyl)-1,1-dimethylurea], or difenzoquat[1,2-dimethyl-3,5-diphenylpyrazolium ion].

The compounds of Formula I may also be combined with other herbicides and are particularly useful in combination with ureas, such as 3-(3,4-dichlorophenyl)-1,1-dimethylurea, 3-(3,4-dichlorophenyl)-1-methoxy-1-methylurea and 1,1-dimethyl-3-($\alpha,\alpha,\alpha$-trifluoro-m-tolyl) urea; the triazines such as 2-chloro-4-(ethylamino)-6-(isopropylamino)-s-triazine; the uracils such as 5-bromo-3-sec-butyl-6-methyluracil; N-(phosphonomethyl)glycine; 3-cyclohexyl-1-methyl-6-dimethylamino-s-triazine-2,4(1H,3H)-dione; N,N-dimethyl-2,2-diphenylacetamide; 2,4-dichlorophenoxyacetic acid (and closely related compounds); 4-chloro-2-butynyl-3-chlorophenylcarbamate; diisopropylthiolcarbamic acid, S-(2,3,3-trichloroallyl)ester; ethyl-N-benzoyl-N-(3,4-dichlorophenyl)-2-aminopropionate; 4-amino-6-tert-butyl-3-(methylthio)-1,2,4-triazin-5(4H)-one; 3-isopropyl-1H-2,1,3-benzothiodiazin-(4)-3H-one-2,2-dioxide; $\alpha,\alpha,\alpha$-trifluoro-2,6-dinitro-N,N-dipropyl-p-toluidine; 1,1'-dimethyl-4,4'-bipyridinium ion; monosodium methanearsonate; and 2-chloro-2',6'-diethyl(methoxymethyl)acetanilide.

The herbicidal properties of the subject compounds were discovered in a number of greenhouse tests. The test procedures and results follow.

Results from the tests are expressed in terms of plant response ratings which are composed of a number and a letter. The number describes the extent of the response and ranges from zero to ten with zero representing no response and ten representing 100% response. The letter describes the type of the response, as explained below.

A=growth acceleration
U=unusual pigmentation

C = chlorosis or necrosis
D = defoliation
E = emergence inhibition
G = growth retardation
H = formative effects The ratings "6Y" and "6F" are exceptions to the above described rating system, and represent abscised buds or flowers and delayed flowering, respectively.

Test Procedure A

Seeds of crabgrass (Digitaria spp.), barnyardgrass (*Echinochloa crusgalli*), wild oats (*Avena fatua*), cassia (*Cassia tora*), morningglory (Ipomoea spp.), cocklebur (Xanthium spp.), sorghum, corn, soybean, rice, wheat and nutsedge tubers (*Cyperus rotundus*) were planted in a growth medium and treated pre-emergence with a nonphytotoxic solvent solution of the compounds of Table A. At the same time, cotton having five leaves (including cotyledonary ones), bush beans with the third trifoliate leaf expanding, crabgrass with two leaves, barnyardgrass with two leaves, wild oats with two leaves, cassia with three leaves (including cotyledonary ones), morningglory with four leaves (including cotyledonary ones), cocklebur with four leaves (including the cotyledonary ones), sorghum with four leaves, corn with four leaves, soybean with two cotyledonary leaves, rice with three leaves, wheat with one leaf, and nutsedge with three to five leaves were sprayed with a nonphytotoxic solvent solution of the compounds of Table A. Other containers of the above mentioned weeds and crops were treated pre- or post-emergence with the same nonphytotoxic solvent so as to provide a solvent control. A set of untreated control plants was also included for comparison. Preemergence and post-emergence treated plants and controls were maintained in a greenhouse for sixteen days, then all treated plants were compared with their respective controls and rated visually for response to treatment. The data in Table A shows that the compounds of this invention are very effective as herbicides and often are capable of modifying plant growth.

TABLE A

| Compound | kg/ha | BUSH-BEAN | COTTON | MORN-ING-GLORY | COCK-LE-BUR | CAS-SIA | NUT-SEDGE | CRAB-GRASS | BARN-YARD-GRASS | WILD OATS | WHEAT | CORN | SOY-BEAN | RICE | SOR-GHUM |
|---|---|---|---|---|---|---|---|---|---|---|---|---|---|---|---|
| POST-EMERGENCE | | | | | | | | | | | | | | | |
| Structure 1 (CH₃O-pyrimidine, Cl) | 0.4 | 9C | 2C,8G | 2C,9G | 5G | 2C,5G | 5G | 4G | 2C,7H | 0 | 0 | 1C,3H | 4C,9G | 3C,8G | 8H |
| Structure 2 (CN-pyrimidine, Cl) | 0.4 | 3C,7G, 6Y | 5C,9G | 5C,9G | 5C,9G | 2C,9H | 8G | 5G | 8H | 0 | 1C,3G | 2C,6H | 2C,8G | 9G | 2H,9G |
| Structure 2 | 2 | 6D,9G, 6Y | 4C,9G | 5C,9G | 9C | 1C,9H | 9G | 1C,8H | 9H | 3G | 2C,7G | 2C,9H | 5H,8G | 2C,9G | 9G |
| Structure 3 (Cl-pyrimidine, CH₂Cl) | 2 | 1C,5G | 1H | 2G | 2G | 3G | 2G | 1C,3G | 5C,9G | 1C | 1C | 5C,6H | 3G | 9C | 5C,9G |
| Structure 4 (Cl-pyrimidine, OCH₃, CH₂Cl) | 2 | 3C,4H, 1C 6Y | | 5C | 9C | 7G | 1C,8G | 2C,5G | 1C,4H | 0 | 0 | 2C,6H | 2C | — | 1C,9G |
| Structure 5 (F-pyrimidine, OCH₃) | 2 | 9D,9G, 2H,4C, 6Y 9G | | 5C,9G | 3C,9H | 3C,9G | 4C,9G | 0 | 3C,8H | 1C | 1C | 5C,9G | 9C | 9C | 2C,8G |

TABLE A-continued

| Structure | | | | | | | | | | | | | | | |
|---|---|---|---|---|---|---|---|---|---|---|---|---|---|---|---|
| ![structure with OCH3, F, OCH3, CO2CH3, SO2NHCNH] | 2 | 7D,9G, 7C,9G 6Y | 7C,9G | 9C | 9C | 2C,5G | 9C | 3C,6H | 3C,5H | 7U,9G | 5C,9G | — | 3U,5C, 9G |
| ![structure with OCH3, F, OCH3, CO2CH2CH=CH2, SO2NHCNH] | 2 | 0 | 0 | 0 | 0 | 0 | 2C | 0 | 0 | 0 | 0 | 1C | 2C |
| ![structure with Cl, CO2CH3, SO2NHCNH] | 2 | 6D,9G, 6Y | 4C,9G 5C,9G | 9C | 1C,9H 2C,9H | 1C,8H 5G | 9H | 3G | 0 | 2C,9H 2C,6H | 2C,9G 5H,8G | 2C,9G | 9G |
| ![structure with CH3, OCH3, CO2CH3, SO2NHCNH] | 2 | 3C,7G, 6Y | 5C,9G 5C,9G | 5C,9G | 9G 8G | 8H | 0 | 1C,3G | 0 | 2C,6H 2C,8G | 9G | 2H,9G |
| ![structure with Br, CH3, CO2CH3, SO2NHCNH] | 0.4 | 9C | 2C,8G 2C,9G | 5G | 2C,5G 4G | 2C,7H | 0 | 0 | 1C,3H | 4C,9G | 3C,8G | 8H |
| ![structure with CH3, CH3, CO2CH3, SO2NHCNH] | 0.4 | 9C | 3C,8G 1C | 9C | 2C,5H 5C,8G | 2C,5H | 0 | 0 | 8H | 2C,9G 1C,9G | 2H,9G |
| ![structure with Cl, CH3, OCH3, CO2CH3, SO2NHCNH] | 0.4 | 9C | 3C,9G 9C | 9C | 2C,7G 9C | 2C,7G | 9C | 2C,9G | 8U,9G | 5C,9G 9C | 9C |
| ![structure with Cl, CH3, CO2CH3, SO2NHCNH] | 0.4 | 7C,9G, 3U,5C, 2C,8G 6Y 9G | | 6C,9G | 10C | 2C,7H | 5C,9G | 9G | 1C,8G | 1C,9G | 5C,8G | — | 5U,9G |

TABLE A-continued

| Structure | | | | | | | | | | | | | | |
|---|---|---|---|---|---|---|---|---|---|---|---|---|---|---|
| ![structure 1] | 0.4 | 7C,9G | 9C | 9C | 9C | 8C,9G | 6C,9G | 9C | 2C,5G | 8U,9G | 6C,9G | 3C,9G | 9C | |
| ![structure 2] | 0.4 | 9C | 3C,4H, 9G | 3C,9G | 4C,9G | 3C,7G 2C,9G | 3G | 9H | 0 | 2C,8H | 3H,9G | 1C,8G | 2C,9H | |
| ![structure 3] | 0.4 | 9C | 6C,9G | 9C | 5C,9G | 3C,4H 1C,9G | 3G | 3C,9H | 2G | | 2C,9H | 4C,9G | 9C | 1C,9G |
| ![structure 4] | 0.4 | 9C | 3C,4H, 10C | 9C | 5C,9G | 2C,6G 1C,7G | 3G | 1C,5H | 0 | 1C,4H | 3H,9G | 1C,2G | 2C,9H |
| ![structure 5] | 0.4 | 10D, 9G | 3C,7G | 3C,8G | 9C | 1C 2G | 3G | 3H | 0 | | | | |
| ![structure 6] | 0.4 | 9D,9G, 6Y | 9C | 9C | 2C,2H, 7G | 6D,7G 9G | 1C,8G | 4C,9G | 1C,7G 4C,8G | 2C,8H | 3C,7G | 5C,9G | 1C,7G 9G |
| ![structure 7] | 0.4 | 6C,9G, 6Y | 2C,3H, 9G | 9C | 2C,2H, 7G | 6D,7G 9G | 1C,6G | 2C,9G | 6G 2C,6G | 1U,8G | 1C,4G | 1C,7G 9G |

TABLE A-continued
| Structure | | | | | | | | | | | |
|---|---|---|---|---|---|---|---|---|---|---|---|
| 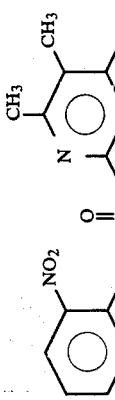 | 0.4 | 9C | 2C,3H, 6G | 9C | 1C,5G 9G | 1C,5G | 2C,9H | 0 | 0 | 1C,9H | 9C | 2C,9G | 1C,7G |
| 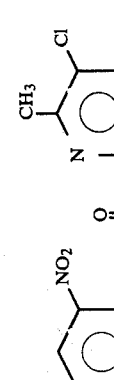 | 0.4 | 9C | 5C,9G 2C,8G | 9C | 2C,5G 1C,7G | 5G | 3C,9H | 0 | 0 | 10C | 9C | 3C,9G | 1C,9H |
| 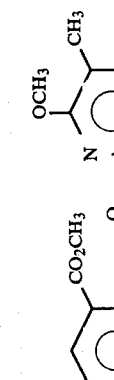 | 0.4 | 3C,9D, 9G | 3C,3H, 4C,9G 9G | 3C,9H | 2C,4G 2C,8G | 3C | 3C,9H | 0 | 0 | | | | |
| 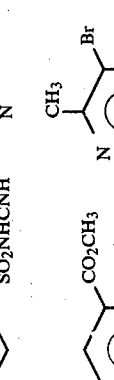 | 0.4 | 9C | 6C,9G 3C,9G | 3C,9G | 5C,9G 1C,6G | 1C | 1C,6H | 0 | 0 | 2C,8H | 2C,9G | 5C,9G | 2C,9G |
| 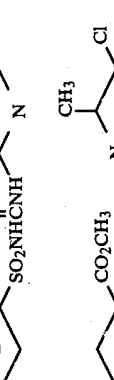 | 0.4 | 8D,9G, 6Y | 8D,9G, 4C,8D, 5C,9G 9G | 6C,9G | 6C,9G 5C,8G | — | 3C,7H | 0 | 0 | 1C,4G | 10C | 7G | 1C,8G |
| 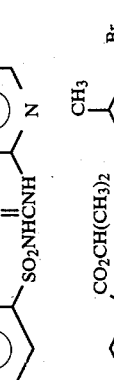 | 0.4 | 8D,9G, 6Y | 2C,3H, 10C 9G | 5C,9G | 2C,2G 0 | 0 | 2G | 0 | 0 | 1C | 9C | — | 2U,9G |
| 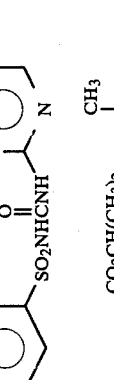 | 0.4 | 10D, 9G,6Y | 2C,3H, 10C 9G | 3C,9G | 2C,3G 1C,3G | 1C | 1C | 0 | 0 | 1C,3G | 1C,3H | 2G | 2G |
| 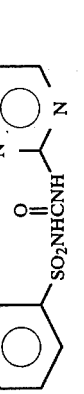 | 0.4 | | | | | | | | | 1C,3G | 2C,8H | 1C,4G | 7G |

TABLE A-continued

| Compound | Rate | | | | | | | | | | | | |
|---|---|---|---|---|---|---|---|---|---|---|---|---|---|
| CH₃, CH₂CH=CH₂, CH₃ pyrimidine with CO₂CH₃, SO₂NHCNH phenyl | 0.4 | 5C,7G | 2C | 1C,5G | 1C | 1C | 1C | 1C,4G | 2C | 0 | 0 | 1C,4H | 1C,5H | 1C,8G |
| CH₃, CH₂CH₂CH₂CH₃, CH₃ | 0.4 | 3C,3H, 6Y | 2C,2H | 3C,3H | 2C | 1C | 0 | 0 | 0 | 0 | 0 | 1C | — | 1C,3H |
| CH₃, CH₂CH₂CH₃, CH₃ | 0.4 | 2C,2H, 6Y | 2C,2H | 1C,4G, 6F | 1C,1H | 1C | 0 | 2G | 1G | 0 | 0 | 0 | — | 1C,4G |
| OCH₃, Br, CH₃ | 0.4 | 6C,7G, 6Y | 3C,3H, 9G | 3C,9H | 3C,8H | 2C | 1C,2G | 3C,9H | 2C,4G | 2C,4G | 5U,9G | 5U,9G | 1U,9G |
| OCH₃, Cl, CH₃ | 0.4 | 8D,9G, 6Y | 2C,2H, 8G | 2H,9G | 2C,5G | 0 | 0 | 0 | 2C,4G | 2C,4G | 1C | 2C,9G | — | 2C,8H |
| OCH₃, Br, OCH₃ | 0.4 | 1C | 2C,5G | 2C | 1C | 0 | 1C | 0 | 1C | 0 | 0 | 1C,4G | 7G | 0 |
| OCH₃, Cl, OCH₃ | 0.4 | 2C,1H | 3C,8G | 1C,5G | 1C | 0 | 0 | 0 | 2G | 0 | 0 | 0 | — | 0 |

TABLE A-continued

| Compound | kg/ha | MORNING-GLORY | COCKLE-BUR | CASSIA | NUT-SEDGE | CRAB-GRASS | BARNYARD-GRASS | WILD OATS | WHEAT | CORN | SOY-BEAN | RICE | SOR-GHUM |
|---|---|---|---|---|---|---|---|---|---|---|---|---|---|
| (structure: pyridine with SO₂NHCNH, Cl) | 0.4 | 3C,8G, 6Y | 3C,8G, 9G | 2C,3H, 9G | 0 | 2C,7G, 5X | 3G | 0 | 0 | 0 | 2H | 1C | 0 |
| (structure: pyridine with CH₃, C₂H₅, CO₂CH₃, SO₂NHCNH, Cl) | 0.4 | 4C,9G, 6Y | 4C,9G | 4C,9H | 0 | 1C,4G | 1C,9G | 2C,9H | 0 | 0 | 2G | 9C | 1C,9G | 1C,9H |

PRE-EMERGENCE

| Compound | kg/ha | MORNING-GLORY | COCKLE-BUR | CASSIA | NUT-SEDGE | CRAB-GRASS | BARNYARD-GRASS | WILD OATS | WHEAT | CORN | SOY-BEAN | RICE | SOR-GHUM |
|---|---|---|---|---|---|---|---|---|---|---|---|---|---|
| (structure: benzoate with NH-C-NH-SO₂, pyrimidine OCH₃, CH₃, Cl) | 0.4 | 6G | 6G | 8G | 9G | 0 | 2C,9H | 2G | 2G | 1C,8G | 2H | 9H | 9H |
| (structure: benzoate with NH-C-NH-SO₂, triazine OCH₃, Cl) | 0.4 2 | — 9G | 9G 9G | 5C,9G 3C,9G | 10E 10E | 3G 6G | 8H 9H | 8G 9H | 2C,9G 9H | 1C,9G 2C,9G | 1C,3G 2C,8H | 10E 10E | 9G 9H |
| (structure: pyrimidine Cl, CH₂CH₂Cl, CO₂CH₃, SO₂NHCNH) | 2 | 3G | 10E | 3G | 5G | 2C,5G | 2C,7G | 1C | 1C | 2C,5G | 2H | 9H | 9H |
| (structure: pyrimidine Cl, CH₂CH₂Cl, OCH₃, CO₂CH₃, SO₂NHCNH) | 2 | 9G | 9H | 9G | 10E | 3G | 2C,6G | 1C,3G | 1C | 2C,8G | 1C,1H | 10E | 3C,9H |

TABLE A-continued

| Structure | | | | | | | | | | | | | |
|---|---|---|---|---|---|---|---|---|---|---|---|---|---|
| ![structure with OCH3, F, OCH3, Cl, CO2CH3, SO2NHCNH] | 2 | 9G | 9G | 2C,9G | 10E | 1C,5G | 9H | 7G | 1C | 9G | 9H | 10E | 2C,7G |
| ![structure with OCH3, F, OCH3, CO2CH3, SO2NHCNH] | 2 | 9G | 9H | 9G | 10E | 3C,9G | 9H | 9H | 9H | 10E | 9H | 10E | 2C,9H |
| ![structure with OCH3, F, OCH3, CO2CH2CH=CH2, SO2NHCNH] | 2 | 0 | — | 0 | 0 | 0 | 0 | 0 | 0 | 0 | 0 | 0 | 0 |
| ![structure with Cl, OCH3, CO2CH3, SO2NHCNH] | 2<br>0.4 | 9G<br>— | 9G<br>9G | 3C,9G<br>5C,9G | 10E<br>10E | 6G<br>3G | 9H<br>8H | 9H<br>8G | 9H<br>2C,9G | 2C,9G<br>1C,9G | 2C,8H<br>1C,3G | 10E<br>10E | 9H<br>9G |
| ![structure with CH3, Cl, OCH3, CO2CH3, SO2NHCNH] | 0.4 | 6G | 6G | 8G | 9G | 0 | 2C,9H | 2G | 2G | 1C,8G | 1C,8G | 9H | 9H |
| ![structure with Br, CH3, OCH3, CO2CH3, SO2NHCNH] | 0.4 | 4G | 2C,9G | 2C,9G | 9G | 0 | 2C,8H | 2G | 0 | 9H | 5G | — | 2C,9H |
| ![structure with CH3, CH3, CH3, CH3, CO2CH3, SO2NHCNH] | 0.4 | 9G | 9G | 9G | 10E | 2G | 9H | 9G | 9G | 10E | 9H | — | 8C,9H |

TABLE A-continued

| Structure | | | | | | | | | | | | | | | |
|---|---|---|---|---|---|---|---|---|---|---|---|---|---|---|---|
| CO2CH3, Cl, CH3, CH3 pyridine; SO2NHCNH | 0.4 | 9G | 9G | 9G | 10E | 2G | 2C,9H | 9G | 9G | 9G | 9H | 10E | 10H |
| CO2CH3, CH2CH3, CH3, CH3 pyridine; SO2NHCNH | 0.4 | 9G | 9H | 8G | 10E | | 9H | 9H | 9H | 9H | 9H | 10E | 1C,9H |
| CO2CH(CH3)2, CH3, CH3, CH3 pyridine; SO2NHCNH | 0.4 | 9G | 9H | 9G | 9G | 1C | 3C,9H | 2C,8G | 2C,8G | 2C,8H | 1C,2H | 9H | 1C,8G |
| CO2CH(CH3)2, Cl, CH3, CH3 pyridine; SO2NHCNH | 0.4 | 9G | 9H | 9G | 10E | 0 | 3C,9H | 1C,5G | 5G | 9H | 9H | 9H | |
| CO2CH2CH=CH2, Cl, CH3, CH3 pyridine; SO2NHCNH | 0.4 | 6G | 9H | 2C,6G | 1C,8G | 2G | 2G | 0 | 0 | 1C,7H | 6H | 7H | 2C,5H |
| CO2CH2CH=CH2, CH3, CH3, CH3 pyridine; SO2NHCNH | 0.4 | 6G | 8G | 5G | 3G | 2G | 4C | 4G | 4G | 2G | 3G | 3G | 2C |
| CO2CH3, I, CH3, CH3 pyridine; SO2NHCNH | | 8G | 9H | 8G | 10E | 2C,8G | 9H | 1C,7G | 1C,8G | 1U,9G | 1U,9G | 5H | 10E | 1U,9G |

TABLE A-continued

| Structure | | | | | | | | | | | | | |
|---|---|---|---|---|---|---|---|---|---|---|---|---|---|
| Phenyl with CO₂CH(CH₃)₂ and SO₂NHC(O)NH-pyridine(CH₃, I, CH₃) | 0.4 | 6G | 8G | 2C | 1C,7G | 2G | 2C,6G | 2G | 1C,7G | 2A | 2C,9H | 1C,8G | |
| Phenyl with NO₂ and SO₂NHC(O)NH-pyridine(CH₃, CH₃, CH₃) | 0.4 | 9G | 9H | 8H | 10E | 0 | 1C,5G | 6G | 1C,6G | 5H | 8H | 0 | |
| Phenyl with NO₂ and SO₂NHC(O)NH-pyridine(CH₃, Cl, CH₃) | 0.4 | 9G | 9H | 8G | 10E | 1G | 9H | 4G | 9H | 9H | 10E | 9H | |
| Phenyl with CO₂CH₃ and SO₂NHC(O)NH-pyridine(OCH₃, CH₃) | 0.4 | 9G | 9H | 8G | 10E | 2G | 3C,9H | 6G | 9H | 5H | 10E | 5C,9H | |
| Phenyl with CO₂CH₃ and SO₂NHC(O)NH-pyridine(CH₃, Br) | 0.4 | 9G | 9G | 3C,9G | 2C,9G | 2G | 2C,9H | 1C,7G | 5G | 9H | 10E | 1C,8G | |
| Phenyl with CO₂CH₃ and SO₂NHC(O)NH-pyridine(CH₃, Cl) | 0.4 | 9G | 8H | 9G | 10E | 4G | 3C,9H | 1C | 1C,6G | 9H | 10E | 9H | |
| Phenyl with CO₂CH(CH₃)₂ and SO₂NHC(O)NH-pyridine(CH₃, Br) | 0.4 | 5G | 8H | 1C | 10E | 1C,5G | 0 | 3G | 7G | 9H | 10E | 1C | |
| | | | | | 0 | 0 | 0 | | 3H | 1C,5G | 1C | | |

TABLE A-continued

| Structure | | | | | | | | | | | | | |
|---|---|---|---|---|---|---|---|---|---|---|---|---|---|
| Pyridine with CH₃, Cl, CO₂CH(CH₃)₂; phenyl-SO₂NHCNH | 0.4 | 8G | 8H | 7G | 4G | 0 | 2C | 0 | 0 | 1C,3G | 6H | 3C | 0 |
| Pyridine with CH₃, CH₂CH=CH₂, CH₃, CO₂CH₃; phenyl-SO₂NHCNH | 0.4 | 8G | 5H | 1C | 7G | 2G | 1C,3G | 2G | 0 | 2C,6G | 0 | 9H | 1C,5G |
| Pyridine with CH₃, CH₂CH₂CH₂CH₃, CH₃, CO₂CH₃; phenyl-SO₂NHCNH | 0.4 | 5G | 6H | 2C | 2G | 5G | 3C | 0 | 0 | 2C,4G | 1H | 2C,5G | 2C,7G |
| Pyridine with CH₃, CH₂CH₂CH₃, CH₃, CO₂CH₃; phenyl-SO₂NHCNH | 0.4 | 8G | 8H | 1C,3G | 5G | 2G | 2C | 0 | 0 | 1C | 0 | 0 | 3G |
| Pyridine with OCH₃, Br, CH₃, CO₂CH₃; phenyl-SO₂NHCNH | 0.4 | 1C,5G | 2C,8G | 1C | 1C | 2G | 1C,5G | 6G | 7G | 1C,9G | 2C,4G | — | 2C,5G |
| Pyridine with OCH₃, Cl, CH₃, CO₂CH₃; phenyl-SO₂NHCNH | 0.4 | 5G | 8G | 1C | 0 | 0 | 0 | 0 | 2G | 1C,4G | 0 | 3G | 3G |
| Pyridine with OCH₃, Br, OCH₃, CO₂CH₃; phenyl-SO₂NHCNH | 0.4 | 8G | 9G | 6G | 0 | 0 | 1C | 0 | 0 | 2C,4G | 0 | — | 1C,3G |

TABLE A-continued

| Structure | | | | | | | | | | | | |
|---|---|---|---|---|---|---|---|---|---|---|---|---|
| Structure 1: phenyl-CO₂CH₃, SO₂NHCNH, pyrimidine with OCH₃, Cl, OCH₃ | 0.4 | 3G | 5G | 0 | 0 | 3G | 0 | 0 | 0 | 1C,6G | 1H | 0 |
| Structure 2: phenyl-SO₂NHCNH-Cl, pyridine with Cl | 0.4 | 0 | 0 | 0 | 0 | 0 | 0 | 0 | 0 | 0 | 0 | 0 |
| Structure 3: phenyl-CO₂CH₃, SO₂NHCNH, pyrimidine with CH₃, Cl, C₂H₅ | 0.4 | 9G | 9G | 8G | 9G | 1C | 2C,9H | 1C,5G | 1C,8G | 10E | 0 | 0 |
| | | | | | | | | 2C,7G | 2C,8H | 2C,7G | 2C,8H | 10E |
| | | | | | | | | | | | | 2C,8H |

Test B

Two plastic bulb pans were filled with fertilized nd limed Fallsington slit loam soil. One pan was planted with corn, sorghum, Kentucky bluegrass and several grassy weeds. The other pan was planted with cotton, soybeans, purple nutsedge (*Cyperus rotundus*), and several broadleaf weeds. The following grassy and broadleaf weeds were planted: crabgrass (*Digitaria sanguinalis*), barnyardgrass (*Echinochloa crusgalli*), wild oats (*Avena fatua*), johnsongrass (*Sorghum halepense*), dallisgrass (*Paspalum dilatatum*), giant fox-tail (*Setaria faberii*), cheatgrass (*Bromus secalinus*), mustard (*Brassica arvensis*), cocklebur (*Xanthium pennsylvanicum*), pigweed (*Amaranthus retroflexus*), morningglory (*Ipomoea hederacea*), cassia (*Cassia tora*), teaweed (*Sida spinosa*), velvetleaf (*Abutilon theophrasti*), and jimsonweed (*Datura stramonium*). A 12.5 cm diameter plastic pot was also filled with prepared soil and planted with rice and wheat. Another 12.5 cm pot was planted with sugarbeets. The above four containers were treated pre-emergence with several test compounds within the scope of the invention.

Twenty-eight days after treatment, the plants were evaluated and visually rated for response to the chemical treatments utilizing the rating system described previously for Test A. The data are summarized in Table B. Certain compounds from within the scope of the invention have utility for selective weed control in soybeans.

TABLE B
PRE-EMERGENCE ON FALLSINGTON SILT LOAM

| Compound | Rate kg/ha | Crab-grass | Barn-yard-grass | Sor-ghum | Wild Oats | Johnson-grass | Dallis-grass | Giant foxtail | Ky. Blue-grass | Cheat-grass | Sugar-beets | Corn | Mus-tard | Cock-lebur | Pig-weed | Nuts-edge |
|---|---|---|---|---|---|---|---|---|---|---|---|---|---|---|---|---|
| 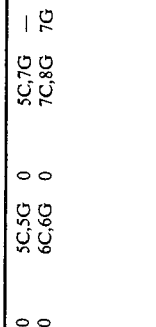 | 1/16<br>1/4 | 0<br>2G | 0<br>3G | 2H<br>5G,3H | 0<br>0 | 0<br>0 | 0<br>0 | 0<br>0 | 0<br>0 | 0<br>0 | 5C,5G<br>6C,6G | 0<br>0 | 5C,7G<br>7C,8G | —<br>7G | 5G<br>10E | 3G<br>8G |
| 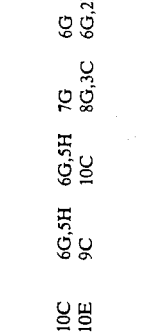 | .062<br>.250 | 0<br>5G | 9G,8C<br>9G,9C | 9G,8C<br>10C | 4G<br>7G,4C | 7G,5H<br>10C | 6G<br>9G,8C | 9G<br>10C | 7G,6C<br>8G,8C | 10C<br>10E | 6G,5H<br>9C | 6G,5H<br>10C | 7G<br>8G,3C | 6G<br>6G,2H | —<br>— | 8G<br>10E |
| 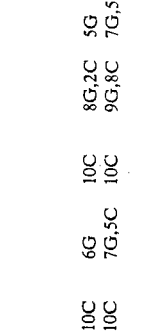 | .031<br>.125 | 6G<br>8G,7C | 8G,4C<br>9G,9C | 10C<br>10E | 7G,2C<br>7G,7C | 8G,8C<br>9G,9C | 9G,8C<br>10C | 8G<br>10C | 8G,7C<br>8G,8C | 10C<br>10C | 6G<br>7G,5C | 10C<br>10C | 8G,2C<br>9G,8C | 5G<br>7G,5H | —<br>— | 10E<br>10E |
| 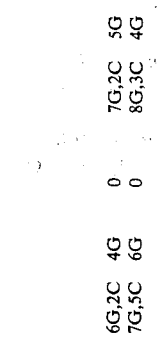 | .062<br>.250 | 0<br>0 | 0<br>6G,3H | 3G<br>7G,5H | 0<br>5G | 0<br>0 | 0<br>0 | 0<br>3G | 4G<br>6G,2C | 6G,2C<br>7G,5C | 4G<br>6G | 0<br>0 | 7G,2C<br>8G,3C | 5G<br>4G | —<br>— | 0<br>7G |
|  | .062<br>.250 | 6G<br>7G | 8G,8C<br>9G,9C | 10C<br>8G,9C | 6G,3C<br>6G,3C | 6G,5H<br>8G,8C | 8G,5C<br>9G,9C | 7G,4C<br>8G,4C | 6G,5C<br>6G,5C | 8G,7C<br>10C | 7G,6C<br>7G,4C | 8G,5H<br>8G,9C | 8G,8C<br>9G,9C | 7G<br>8G,9C | —<br>— | 10E<br>10E |

TABLE B-continued

PRE-EMERGENCE ON FALLSINGTON SILT LOAM

| Compound | Rate | | | | | | | | | | | | | | |
|---|---|---|---|---|---|---|---|---|---|---|---|---|---|---|---|

Structure 1: Pyrimidine with Cl, CH₂—CH=CH₂, Cl substituents; SO₂—NH—C(=O)—NH linker to phenyl with COOCH₃

| Rate | | | | | | | | | | | | | | |
|---|---|---|---|---|---|---|---|---|---|---|---|---|---|---|
| .062 | 0 | 3G | 7G,5H | 0 | 3G,3H | 5G | 4G | 5G,3C | 5G,3H | 0 | 6G | 3G | — | 10E |
| .250 | 2G | 7G,5C | 10E | 2G | 6G,5H | 4G | 3G,2C | 6G,4C | 7G,5H | 6G,3H | 5G,2C | — | — | 10E |

Structure 2: Pyrimidine with CH₃, CH₃, CH₃ substituents; SO₂—NH—C(=O)—NH linker to phenyl with NO₂

| Rate | | | | | | | | | | | | | | |
|---|---|---|---|---|---|---|---|---|---|---|---|---|---|---|
| 0.06 | 0 | 0 | 0 | 0 | 0 | 0 | 0 | 0 | 6G,3H | 0 | 6G | 0 | — | 4G |
| 0.25 | 0 | 0 | 0 | 0 | 0 | 4G | 8G,7C | 6G,3H | 0 | 3C,8G | 6G | — | — | 9G |

Structure 3: Pyrimidine with Cl, CH₂—CH₂Cl, Cl substituents; SO₂—NH—C(=O)—NH linker to phenyl with COOCH₃

| Rate | | | | | | | | | | | | | | |
|---|---|---|---|---|---|---|---|---|---|---|---|---|---|---|
| .031 | 0 | 2G | 8G,5H | 2G,2C | 5G,3H | 7G | 3G | 6G,8C | 7G,8C | 5G | 7G,3C | 3G | — | 0 |
| .062 | 4G | 3G,2C | 3G | 3G,3C | 8G,3C | 7G | 6G,7C | 10C | 6G,8C | 5G,6C | 8G,6C | 5G | — | 7G |
| .125 | 3G | 6G,4C | 10C | 6G,5H | 10C | 10C | 5G,5H | 5G,6C | 7G,3C | 7G,3C | 6G,3C | 6G | — | 8G |
| .250 | 10C | 7G,5H | 9G,9C | 7G,5C | 10C | 10C | 9G,9C | 8G,9C | 10C | 10C | 10C | 7G,5H | — | 9G |
| .5 | 7G,6C | 8G,7C | 10C | 7G,5C | 10E | 10E | 8G,5H | 8G,8C | 8G,8C | 8G,7C | 9G,9C | 6G | — | 10E,UN- |
| .5 | 7G,2C | 7G,8C | 9G,9C | 5G,4C | 8G,7C | 10E | | 8G,5H | 10E | 9G,9C | 9G,9C | 6G,3H | — | 10E |
| 1 | 7G,5C | 9G,8C | | 6G,4C | 10E | 10E | | | 10E | 10E | 6G | — | 10E |

Structure 4: Pyrimidine with CH₃, Cl, CH₃ substituents; SO₂—NH—C(=O)—NH linker to phenyl with NO₂

| Rate | | | | | | | | | | | | | | |
|---|---|---|---|---|---|---|---|---|---|---|---|---|---|---|
| .062 | 0 | 0 | 3G | 0 | 0 | 0 | 0 | 3G | 2G | 0 | 6G | 3G | — | 10E |
| .250 | 3G | 7G,2H | 5G,2H | 0 | 4G | 3G | 4G | 4G | 6G | 5G,3H | 7G,6C | 4G | — | 10E |

Structure 5: Pyrimidine with OCH₃, CH₃, CH₃ substituents; SO₂—NH—C(=O)—NH linker to phenyl with COOCH₃

| Rate | | | | | | | | | | | | | | |
|---|---|---|---|---|---|---|---|---|---|---|---|---|---|---|
| .062 | 0 | 0 | 4G | 0 | 3G | 0 | 5G | 0 | 8G,8C | 0 | 7G,5C | 5G | — | 0 |
| .250 | 3G | 6G,3C | 9G,9C | 2G | 5G | 5G | 6G,2C | 5G,5C | 8G,5C | 5G,2C | 9G,9C | 2G | — | 6G |

Structure 6: Pyrimidine with CH₃, Br, CH₃ substituents; SO₂—NH—C(=O)—NH linker to phenyl with COOCH₃

| Rate | | | | | | | | | | | | | | |
|---|---|---|---|---|---|---|---|---|---|---|---|---|---|---|
| .125 | 4G | 0 | 6G,3H | 0 | 3G | 3G | 0 | 0 | 5G,3C | 0 | 7G,5C | 5G | — | 10E |
| .5 | 6G,3C | 6G,3H | 7G,3H | 0 | 5G | 6G,2C | 5G,3C | 5G,3C | 7G,7C | 4G | 8G,3C | 6G,2C | — | 10E |

TABLE B-continued

PRE-EMERGENCE ON FALLSINGTON SILT LOAM

| Structure | Rate kg/ha | | | | | | | | | | | | |
|---|---|---|---|---|---|---|---|---|---|---|---|---|---|
| ![structure 1: pyrimidine with CH3, Cl substituents] | .125 .5 | 0 4G | 5G 8G,5H | 8G,5H 9G,8C | 6G,3H 7G,3H | 0 5G | 3G 10C | 4G 6G | 5G,3C 6G,5C | 6G,5C 7G,7C | 5G,3C 6G,5C | 0 5G | 8G 9G,8C | 6G,3H 6G,5C | — — | 10E 10E |
| ![structure 2: pyrimidine with Cl] | 0.06 0.25 | 0 2G | 0 3G | 2H 5G,3H | 0 0 | 0 0 | 0 0 | 0 0 | 0 0 | 5G,5C 6G,6C | 0 0 | 0 0 | 7G,5C 8G,7C | 5G 7G | — 10E | 3G 8G |
| ![structure 3: pyrimidine with OCH3, F, OCH3] | 0.015 0.03 0.12 | 3G 3G,2C 6G,2C | 5G,3C 7G,4C 8G,5H | 10C 10C 10E | 4G 5G 7G,3H | 4G 3G,2C 6G | 7G,3H 8G,5H 8G,5C | 5G 8G,9E 10C | 5G 7G,4C 8G,8C | 6G,3C 7G,6C 10C | 6G,3C 6G,3C 8G,7C | 6G,3H 7G,5H 8G,5H | 9G,9C 8G,8C 9G,9C | 6G 6G,3H 8G,5H | — — — | 10E 10E 10E |

| | Rate kg/ha | Cotton | Morning glory | Cassia | Tea weed | Velvet leaf | Jimson weed | Soybean | Rice | Wheat |
|---|---|---|---|---|---|---|---|---|---|---|
| ![structure 4: chloropyrimidine urea sulfonyl benzoate] | 1/16 1/4 | 4G,4H 8G | 5G,3H 7G,5C | 0 5G,7C | 0 3G | 0 5G,4H | 0 2G | 0 2C | 0 3G,3C | 0 0 |
| ![structure 5: trimethylpyrimidine urea sulfonyl benzoate] | .062 .250 | 6G 6G,2H | 0 7G | 5G 7G | — — | 0 5G,3H | 3G,3C 5G,2C | 5G,5H 5G,3H | 10E 10E | 4G 6G |

TABLE B-continued
PRE-EMERGENCE ON FALLSINGTON SILT LOAM

Compound 1: Pyrimidine substituted with CH3, C2H5, CH3; linked via SO2—NH—C(=O)—NH— to phenyl bearing COOCH3

| Rate | | | | | | | | |
|---|---|---|---|---|---|---|---|---|
| .031 | 6G | 5G | 4G | 7G | 5G,3H | 3H | 7G,5H | 6G |
| .125 | 8G | 7G | 6G | 7G | 9G,9C | 5G,5C | 8G | 8G,6C |

Compound 2: Pyrimidine substituted with CH3, CH3, CH3; linked via SO2—NH—C(=O)—NH— to phenyl bearing OCH(CH3)2

| Rate | | | | | | | | |
|---|---|---|---|---|---|---|---|---|
| .062 | 3G | 0 | 3G | 0 | 0 | 0 | 3G | 0 |
| .250 | 6G,5H | 6G | 7G | 5G | 5G,3H | 0 | 7G,3C | 3G,3C |

Compound 3: Pyrimidine substituted with CH3, I, CH3; linked via SO2—NH—C(=O)—NH— to phenyl bearing COOCH3

| Rate | | | | | | | | |
|---|---|---|---|---|---|---|---|---|
| .062 | 8G | 7G,3C | 7G,5C | 8G,4C | 8G,8C | 4G | 5G,6C | 6G,3C |
| .250 | 8G,3C | 8G,4C | 7G,5C | 9G,7C | 10C | 4G | 7G,7C | 6G,4C |

Compound 4: Pyrimidine substituted with Cl, CH2—CH=CH2, Cl; linked via SO2—NH—C(=O)—NH— to phenyl bearing COOCH3

| Rate | | | | | | | | |
|---|---|---|---|---|---|---|---|---|
| .062 | 0 | 0 | 4G | 0 | 2G | 0 | 2G | 7G,5H | 3G |
| .250 | 6G | 4G | 8G,8C | 0 | 5G,3H | 0 | 6G,4H | 10E | 5G |

Compound 5: Pyrimidine substituted with CH3, CH3, CH3; linked via SO2—NH—C(=O)—NH— to phenyl bearing NO2

| Rate | | | | | | | | |
|---|---|---|---|---|---|---|---|---|
| 0.06 | 0 | 0 | 2G | 0 | 0 | 0 | 0 | 0 | 0 |
| 0.25 | 0 | 0 | 0 | 0 | 5G,3H | 0 | 2H | 6G,3H | 0 |

TABLE B-continued
PRE-EMERGENCE ON FALLSINGTON SILT LOAM

| Structure | Rate | | | | | | | | | |
|---|---|---|---|---|---|---|---|---|---|---|
| Cl / CH₂—CH₂Cl / CH₃ pyrimidine with SO₂—NH—C(=O)—NH, COOCH₃ phenyl | .031 | 5G | 0 | 0 | 0 | 0 | 0 | 0 | 8G,8C | 5G,3C |
| | .062 | 2G | 2G | 0 | — | 0 | 3G | 0 | 7G,8C | 6G,3C |
| | .125 | 4G | 0 | 6G,3C | 5G | 5G | 3G | 2G | 10E | 5G |
| | .250 | 7G | 7G,2C | 8G,7C | — | 10C | 8G,8C | 0 | 10E | 7G,5C |
| | .5 | 7G | 6G | 8G,6C | 5G,3C | 6G,5H | 5G | 6G | 10C | 8G,5H |
| | .5 | 7G | 6G | 6G | 3G | 6G,5C | 3G | 5G,3H | 10C | 8G,7C |
| | 1 | 8G | 7G | 9G,9C | 10E | 6G,5H | 5G | 5G,3H | 10E | 5G,3C |
| CH₃ / Cl / CH₃ pyrimidine with SO₂—NH—C(=O)—NH, NO₂ phenyl | .062 | 0 | 0 | 0 | 0 | 4G | 0 | 0 | 7G,5E | 0 |
| | .250 | 3G | 4G | 6G | 4G | 6G,3H | 0 | 4G,3H | 9G,9C | 2G |
| OCH₃ / CH₃ pyrimidine with SO₂—NH—C(=O)—NH, COOCH₃ phenyl | .062 | 0 | 0 | 0 | — | 0 | 0 | 0 | 5G | 0 |
| | .250 | 0 | 3G | 3G | — | 5G | 0 | 5G,5H | 7G,4C | 2G |
| CH₃ / Br / pyrimidine with SO₂—NH—C(=O)—NH, COOCH₃ phenyl | .125 | 5G | 0 | 3G | 6G,2C | 5H | 0 | 6G,3H | 6G,6C | 0 |
| | .5 | 7G | 6G,3H | 6G | 8G,8C | 6G,8C | 3G | 7G,7H | 10C | 2G |
| CH₃ / Cl / pyrimidine with SO₂—NH—C(=O)—NH, COOCH₃ phenyl | .125 | 7G | 4G | 7G | 6G,5C | 5H | 0 | 8G,8H | 10C | 0 |
| | .5 | 8G | 6G | 8G,8C | 9G,9C | 9G,9C | 4G | 8G,8C | 10E | 3G |
| CH₃ / Cl / pyrimidine with SO₂—NH—C(=O)—NH, COOCH₃ phenyl | 0.06 | 4G,3H | 5G,3H | 5G,7C | 0 | 0 | 0 | 0 | 0 | 0 |
| | 0.25 | 8G | 7G,5C | 5G,7C | 3G | 5G,4H | 2G | 2C | 3G,3C | 0 |

TABLE B-continued
PRE-EMERGENCE ON FALLSINGTON SILT LOAM
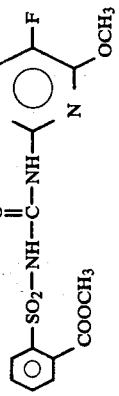
| | | | | | | | | |
|---|---|---|---|---|---|---|---|---|
| 0.015 | 4G | 8G | 6G | 8G,8C | 5G,5H | 7G,5C | 8G,5H | 10E | 3G |
| 0.03 | 6G | 8G | 7G | 8G,8C | 8G,8C | 5G,5C | 8G,8H | 10C | 4G |
| 0.12 | 8G | 8G,5C | 8G,8C | 9G,8C | 10C | 6G,5C | 8G,9C | 10E | 6G |

Test C

Twenty-five cm diameter plastic pots filled with Fallsington silt loam were planted to soybeans, cotton, alfalfa, corn, rice, wheat, sorghum, velvetleaf (*Abutilon theophrasti*), sesbania (*Sesbania exaltata*), Cassia (*Cassia tora*), morningglory (*Ipomoea hederacea*), jimsonweed (*Datura stramonium*), cocklebur (*Xanthium pennsylvanicum*), crabgrass (*Digitaria* spp.), nutsedge (*Cyperus rotundus*), barnyardgrass (*Echinochloa crusgalli*), giant foxtail (*Setaria faberii*) and wild oats (*Avena fatua*). Approximately 2½ weeks after planting, the young plants and the soil around them were sprayed overall with the test chemicals dissolved in a nonphytotoxic solvent. Fourteen days after treatment, all species were compared to untreated controls and visually rated for response to treatment. The rating system was as described previously for Test A. The data are presented in Table C.

TABLE C

OVER-THE-TOP SOIL/FOILAGE TREATMENT

| Compound | Rate kg/ha | Soybeans | Velvetleaf | Sesbania | Cassia | Cotton | Morningglory | Alfalfa | Jimsonweed | Cocklebur |
|---|---|---|---|---|---|---|---|---|---|---|
| Cl-pyrimidine(H,H)-NH-CO-NH-SO2-Ph(CH3O-CO) | 1/16<br>1/4 | 4C,8G<br>8C,<br>10G | 6C,<br>10G<br>10C | 5C,8G<br>9C,<br>10G | 5C,8G<br>3C,<br>10G | 3C,9G<br>3C,<br>10 G | 6C,<br>10G<br>10C | 6C,<br>10G<br>6C,<br>10G | 5C,<br>10G<br>5C,<br>10G | 5C,<br>10G<br>5C,<br>10G |
| Cl-pyrimidine(CH3,CH3)-NH-CO-NH-SO2-Ph(CH3OOC) | 1/4<br>1/16 | 10G,<br>8C<br>10G,<br>7C | —<br>— | —<br>— | 10C<br>10C | 10G,<br>4C<br>9G,7C | 9G,7C<br>4G | 8C<br>8C | —<br>— | 10G<br>8C<br>7G,3C |
| CH3,CH3-pyrimidine(CH3)-NH-CO-NH-SO2-Ph(CH3OOC) | 1/8<br>1/32 | 10G,<br>7C<br>10G,<br>6C | 10C<br>9G,1C | 9C<br>10G,<br>7C | 9G,5C<br>8G,4C | 6G,2C<br>5C,1C | 7G,5H<br>10G,<br>7C | 9C<br>8G,3C | 10C<br>5G,2C | 8G,4C<br>3G |
| CH3O,CH3O-pyrimidine(F)-NH-CO-NH-SO2-Ph(Cl) | 1/4<br>1 | 10G,<br>7C<br>8C | 10G,<br>7C<br>10G,<br>6C | 10G,<br>6C<br>10G,<br>8C | 9G,4C<br>10G,<br>5C | 5G,2C<br>7G,2C | 10G,<br>6C<br>10G,<br>8C | 3G,2C<br>8C | —<br>— | 5G,7H<br>9G,4C |
| CH3,CH3-pyrimidine(CH3)-NH-CO-NH-SO2-Ph(Cl) | 1/4<br>1/16 | 5G,2C<br>2G | 10G,<br>2C<br>7G | 8G,2C<br>3G | 4G,1C<br>1G,2C | 4G,2C<br>3G,1C | 10G,<br>4C<br>8G | 2<br>0 | 1C,3G<br>0 | 3G,1C<br>2G |
| CH3O,CH3-pyrimidine(Br)-NH-CO-NH-SO2-Ph(CH2OOC) | 1/16<br>1/64 | 10C<br>7G,4C | 7G,3C<br>1C | 8G,3C<br>0 | 7G,3C<br>3G,1C | 7G,3C<br>2G | 10G,<br>4C | 6C<br>1C | 2G,2C<br>0 | 3G,1C<br>0 |
| CH3O,CH3-pyrimidine(Cl)-NH-CO-NH-SO2-Ph(CH3OOC) | 1/2<br>1/4 | 10G,<br>7C<br>10G,<br>7C | 10C<br>— | —<br>— | 10G,<br>7C<br>10G,<br>6C | 8G,3C<br>8G,4C | 10G,<br>7C<br>4G | 9C<br>8C | —<br>— | 3G,2C<br>0 |

Barn-

TABLE C-continued
OVER-THE-TOP SOIL/FOILAGE TREATMENT

| | Rate kg/ha | Corn | Crab-grass | Rice | Nuts-edge | yard-grass | Wheat | Giant Foxtail | Wild Oats | Sor-ghum |
|---|---|---|---|---|---|---|---|---|---|---|
| 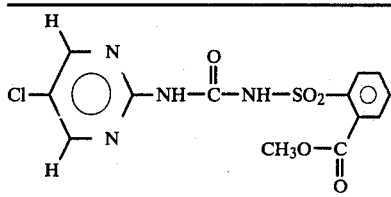 | 1/16 | 5H,8G | 3G | 4C | 0 | 3C, | 6G | 0 | 3G | 8G,2H |
| | 1/4 | 3H,9G | 3G | 10G 3C, 10G | 0 | 10G, 4C, 10G | 10G | 0 | 7G | 10G, 2H |
| 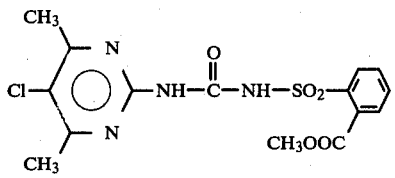 | 1/4 | 9G,5U | 7G | 9G,4C | 4G | 10G, 5C 9G | 4G | — | 10G, 7C 5G,2C | 10C |
| | 1/16 | 9G,7H | 3G | 7G,1C | 8G,2C | | 2G | — | | 8G,3C |
| 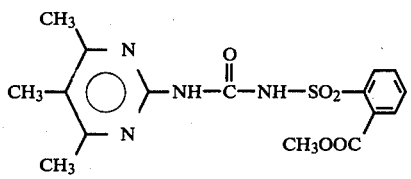 | 1/8 | 5G,2C | 2G | 10C | 8G,3C | 9G,6C | 7G | 5G | 7G | 9G,3C |
| | 1/32 | 7G,5H | 7G,6C | 8G,5C | 7G | 5G,2C | 2G | 0 | 2G | 7G,1C |
| 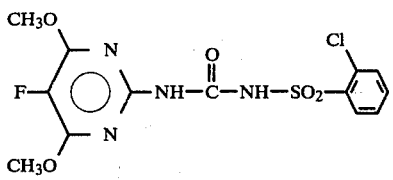 | 1/4 | 5G,7H | 0 | 4G,1C | 10G, 6C 8G,5C | 5G,2C | 0 | 6G | 0 | 6G |
| | 1 | 4G,4H | 1G | 4G,1C | | 6G,3C | 0 | 6G | 0 | 8G |
| 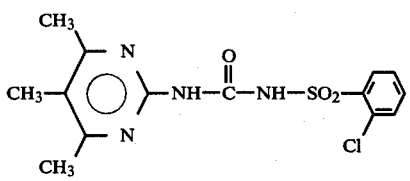 | 1/4 | 3G,1C | 2G,2C | — | 3G | 5G,1C | 0 | 3G | 0 | 9G,3C |
| | 1/16 | 0 | 0 | — | 0 | 0 | 1G | 2G | 0 | 0 |
| 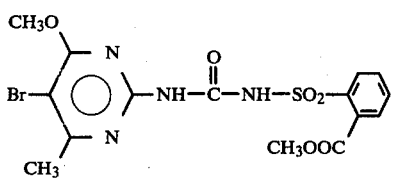 | 1/16 | 8G,2H | 0 | 2G | 5G | 2G,1C | 0 | — | 0 | 8G,3C |
| | 1/64 | 0 | 0 | 0 | 2G | 0 | 0 | — | 0 | 2G,1C |
| 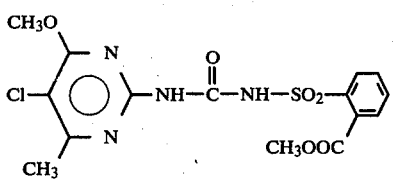 | 1/2 | 4G | — | 3G | 5G | 1C,6G | 0 | — | 3G | 5G,2C |
| | 1/4 | 4G | 5G | 0 | 1G | 3G | 0 | — | 3G | 5G,2C |

Test D

Purple nutsedge (*Cyperus rotundus*) tubers were planted about 2 cm deep in Fallsington silt loam soil contained in 10 cm diameter plastic pots. Five tubers were planted in each pot. Compounds of this invention were dissolved in an nonphytotoxic diluent and sprayed at 560 l/ha in four methods of application: soil surface, tuber/soil, soil incorporated, and post-emergence. The soil surface spray consisted of spraying the compound on the surface of the firmed covering soil. The tuber/soil spray consisted of spraying the compound on exposed tubers and subtending soil before adding the untreated covering soil. Soil incorporated treatment consisted in mixing the compound with the covering soil before using it to cover the tubers. The post-emergence treatment was sprayed on nutsedge foliage and the surrounding soil surface when nutsedge had emerged and grown to a height of about 12 cm. Pots receiving the post-emergence treatments were placed directly in the greenhouse. Pots receiving the other treatments were misted with about 0.3 cm water before being transferred to the greenhouse. Response ratings assessed after four weeks are recorded in Table D based on the same rating system as described in procedure A.

TABLE D

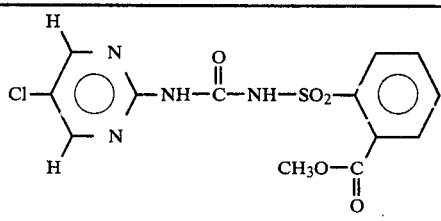

| | Plant Response 4 Weeks after Treatment | | | |
|---|---|---|---|---|
| Rate kg/ha | Pre Surface spray | Pre tuber + soil spray | Pre soil inc. 2.5 cm | Post foliar spray |
| 1/64 | 0 | 3G | 3G | 0 |
| 1/16 | 2G | 8G | 7G | 0 |
| 1/4 | 8G | 9E,9G | 6E,8G | 2C,4G |

Test E

Two ten-inch in diameter plastic pans lined with polyethylene liners were filled with prepared Fallsington slit loam silt. One pan was planted with seeds of wheat (*Triticum aestivum*), barley (*Hordeum vulgare*), wild oats (*Avena fatua*), downy brome (*Bromus tectorum*), cheatgrass (*Bromus secalinus*), blackgrass (*Alopecurus myosuroides*), annual bluegrass (*Poa annua*), green foxtail (*Setaria viridis*), quackgrass (*Agropyron repens*), Italian ryegrass (*Lolium multiflorum*) and ripgut brome (*Bromus rigidus*). The other pan was planted with seeds of Russian thistle (*Salsola Kali*), tansy mustard (*Descurainia pinnata*), smartweed (*Polygonum pennsylvanicum*), jimhill mustard (*Sisymbrium altissimum*), Kochia (*Kochia scoparia*), shepherd's purse (*Capsella bursa-pastoris*), false chamomile (*Matricaria inodora*), black nightshade (*Solanum nigrum*), yellow rocket (*Barbarea vulgaris*), wild mustard (Brassica kaber) and wild buckwheat (*Polygonum convolvulus*). The above two pans were treated pre-emergence. At the same time, two pans in which the above plant species were growing were treated post-emergence. Plant height at the time of treatment ranged from 1–15 cm depending on plant species.

The compounds applied were diluted with a non-phytotoxic solvent and sprayed over-the-top of the pans. An untreated control and a solvent-alone were included for comparison. All treatments were maintained in the greenhouse for 20 days at which time the treatments were compared to the controls and the effects visually rated utilizing the rating system described previously for Test A. The recorded data are presented in Table E. It may be seen that several of the test compounds provide control of a range of weed species without causing injury to wheat or barley.

TABLE E

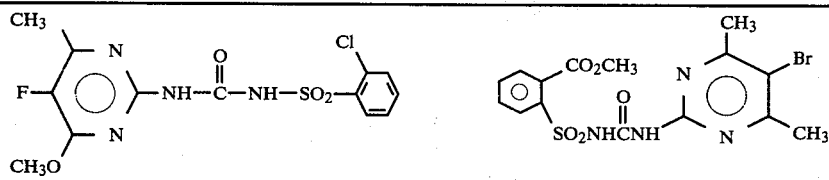

| | Pre-emergence | | Post-emergence | | Pre-emergence | | Post-emergence | |
|---|---|---|---|---|---|---|---|---|
| Rate kg/ha | 1/4 | 1 | 1/4 | 1 | 1/64 | 1/16 | 1/64 | 1/16 |
| wheat | 0 | 0 | 0 | 0 | 0 | 0 | 0 | 0 |
| barley | 0 | 2G | 2G | 3G | 0 | 0 | 0 | 0 |
| wild oats | 0 | 1G | 2C,2G | 2C,3G | 0 | 0 | 0 | 0 |
| downy brome | 7G | 7G | 2C,5G | 3C,4G | 0 | 2G | 0 | 0 |
| cheatgrass | 6G | 7G | 1C,3G | 2C,6G | 2G | 3G | 0 | 0 |
| blackgrass | 6G | 7G | 1C,3G | 2C,5G | 0 | 0 | 0 | 0 |
| annual bluegrass | 7G | 2C,8G | 2C,3G | 2C,5G | 2G | 3G | 0 | 0 |
| green foxtail | 1G | 2C,4G | 3C,3G | 4C,5G | 0 | 0 | 0 | 0 |
| quackgrass | 5G | 7G | 3G | 5G | 0 | 0 | 0 | 0 |
| Italian ryegrass | 5G | 3C,7G | 3G | 3C,7G | 0 | 0 | 0 | 0 |
| ripgut brome | 1G | 2G | 0 | 2G | 0 | 0 | 0 | 0 |
| Russian thistle | 3C,2G | 4C,5G | 9C,7G | 10C | 0 | 0 | 0 | 2C,2G |
| tansy mustard | 9C,9G | 9C,9G | 10C | 10C | 2G | 2C,5G | 10C | 10C |
| smartweed | 9C,9G | 9C,9G | 10C | 10C | 1G | 3G | 1C | 5C,5G |
| jimhill mustard | 8C,9G | 8C,9G | 10C | 10C | 3G | 5C,7G | 10C | 10C |
| Kochia | — | — | 10C | 10C | 0 | 5G | 4G | 10C |
| shepherd's purse | 9C,9G | 10C | 10C | 10C | 3G | 7C,8G | 2C,3G | 3C,5G |
| false chamomile | 7C,8G | 7C,9G | 9C,9G | 10C | 0 | 2C,4G | 2C,2G | 5C,5G |
| black nightshade | 2C,7G | 3C,8G | 2C,4G | 5C,7G | — | — | — | — |
| yellow rocket | 7C,8G | 7C,9G | 10C | 10C | 5G | 5C,7G | 10C | 10C |
| wild mustard | 7C,8G | 7C,9G | 10C | 10C | 0 | 5C,4G | 10C | 10C |
| wild buckwheat | 2C,4G | 3C,7G | 5C,4G | 5C,5G | 0 | 1C,2G | 0 | 0 |

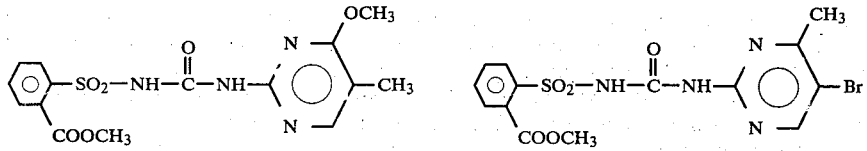

| | Pre-emergence | | Post-emergence | | Pre-emergence | | Post-emergence | |
|---|---|---|---|---|---|---|---|---|
| Rate kg/ha | 1/64 | 1/16 | 1/64 | 1/16 | 1/64 | 1/16 | 1/64 | 1/16 |

TABLE E-continued

| | Pre-emergence | | Post-emergence | | Pre-emergence | | Post-emergence | |
|---|---|---|---|---|---|---|---|---|
| Rate kg/ha | 1/64 | 1/16 | 1/64 | 1/16 | 1/64 | 1/16 | 1/64 | 1/16 |
| wheat | 0 | 0 | 0 | 0 | 0 | 0 | 0 | 0 |
| barley | 0 | 0 | 0 | 2C,4G | 0 | 0 | 0 | 0 |
| wild oats | 0 | 0 | 0 | 0 | 0 | 0 | 0 | 0 |
| downy brome | 0 | 0 | 0 | 2G | 0 | 0 | 0 | 0 |
| cheatgrass | 0 | 3C,4G | 0 | 2C,3G | 0 | 2G | 1G | 2G |
| blackgrass | 0 | 2C,3G | 0 | 2C | — | — | 0 | 1G |
| annual bluegrass | 1G | 2C,2G | 0 | 2C,2G | 0 | 1G | 0 | 1G |
| green foxtail | 0 | 0 | 0 | 9C | 0 | 0 | 2G | 1C,3G |
| quackgrass | 0 | 2G | 0 | 0 | 0 | 0 | 3G | 4C,5G |
| Italian ryegrass | 0 | 0 | 0 | 0 | 0 | 0 | 0 | 3G |
| ripgut brome | 0 | 0 | 0 | 1G | 0 | 0 | 0 | 0 |
| Russian thistle | 0 | 2C,3G | 2C | 7C | 0 | 1G | 0 | 10C |
| tansy mustard | 2G | 10C | 2C,3G | 9C | 2C,3G | 7C,8G | 0 | 5C,5G |
| smartweed | — | — | 2C,2G | 8C | — | — | 0 | 8C |
| jimhill mustard | 5C,6G | 6C,7G | 7C | 9C | 4G | 7G | 0 | 7C |
| Kochia | 4G | 3C,5G | 3C,5G | 5C,5G | 0 | 3G | 1C | 7C |
| shepherd's purse | 5C,7G | 5C,8G | 2G | 3C,5G | 5G | 8C,9G | 0 | 10C |
| false chamomile | 1G | 4C,3G | 2C,2G | 2C | 1C,2G | 7C,8G | 1C | 5C,3G |
| black nightshade | — | — | — | — | — | — | — | — |
| yellow rocket | 2G | 5C,7G | 0 | 1C,2G | 2G | 3C,7G | 0 | 2C |
| wild mustard | 1G | 7C,7G | 2C,3G | 6C,5G | 4G | 7G | 0 | 7C,6G |
| wild buckwheat | 0 | 0 | 0 | 2C | 0 | 0 | 0 | 1C |

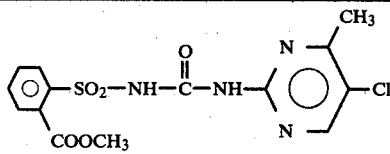  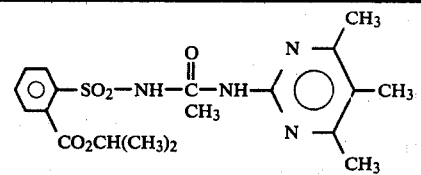

| | Pre-emergence | | Post-emergence | | Pre-emergence | | Post-emergence | |
|---|---|---|---|---|---|---|---|---|
| Rate kg/ha | 1/64 | 1/16 | 1/64 | 1/16 | 1/64 | 1/16 | 1/164 | 1/16 |
| wheat | 0 | 0 | 0 | 0 | 0 | 0 | 0 | 0 |
| barley | 0 | 0 | 0 | 1C,1G | 0 | 1G | 2G | 4C,7G |
| wild oats | 0 | 0 | 0 | 2C | 0 | 0 | 0 | 0 |
| downy brome | 0 | 2G | 0 | 1C,3G | 1G | 2G | 0 | 0 |
| cheatgrass | 2G | 1C,3G | 1G | 1C,4G | 2G | 5G | 0 | 2G |
| blackgrass | — | — | 1C,2G | 1C,3G | — | — | 1C,1G | 2C,3G |
| annual bluegrass | 0 | 1G | 0 | 0 | 2C,3G | 2C,5G | 0 | 1C,2G |
| green foxtail | 0 | 1C | 1C,2G | 0 | 0 | 0 | 1G | 1C,3G |
| quackgrass | 0 | 0 | 3C,4G | 2C,3G | 0 | 3G | 1G | 2G |
| Italian ryegrass | 0 | 2G | 5C,4G | 1G | 2G | 3G | 2G | 2C,5G |
| ripgut brome | 0 | 0 | 0 | 0 | 0 | 2G | 0 | 2G |
| Russian thistle | 0 | 1C,2G | 9C | 10C | 0 | 2C,3G | 0 | 3C,5G |
| tansy mustard | 2C,3G | 9C | 1C,2G | 4C,5G | 8C | 10C | 0 | 3C |
| smartweed | — | — | 7C | 8C | — | — | — | — |
| jimhill mustard | 8C | 9C | 5C,6G | 7C,7G | 9C | 10C | 0 | 6C,5G |
| Kochia | 3G | 1C,5G | 6C,7G | 8C | 0 | 2G | 0 | 0 |
| shepherd's purse | 9C | 10C | 4C,3G | 5C,7G | 3C,7G | 7C,8G | 3C | 3C,5G |
| false chamomile | 7C,8G | 8C,9G | 5C,3G | 7C,5G | 1C,2G | 6C,7G | 0 | 4C,5G |
| black nightshade | — | — | — | — | — | — | — | — |
| yellow rocket | 7C,7G | 8C,9G | 7C | 7C,7G | 7G | 7C,8G | 0 | 3C |
| wild mustard | 2C,7G | 3C,7G | 2C,5G | 6C,5G | 2G | 5C,6G | 1C | 5C,4G |
| wild buckwheat | 0 | 1G | 1C | 2C,3G | 0 | 2C,6G | 0 | 2C,3G |

What is claimed is:

1. A compound selected from:

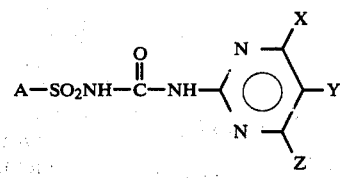

wherein
A is

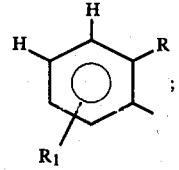

R is $CO_2R^2$,

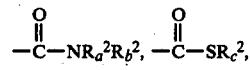

$SO_2NR^3R^4$, Cl, $CF_3$, $NO_2$ or $S(O)_nR^3$ where n is 0, 1 or 2;

$R^1$ is H, Cl, F, Br, $NO_2$, $CH_3$, $OCH_3$ or $CF_3$;

$R^2$ is $C_1$–$C_6$ alkyl, $C_3$–$C_4$ alkenyl, $C_2$–$C_3$ haloalkyl, $C_5$–$C_6$ cycloalkyl, $C_4$–$C_7$ cycloalkylalkyl, $CH_2OCH_2CH_2OCH_3$, $CH_2$—$CH(CH_3)OR^5$ or $(CH_2)_mOR^5$ where m is 1, 2 or 3;

$R_a{}^2$ is H, $C_1$–$C_4$ alkyl, $C_3$–$C_4$ alkenyl or $OCH_3$;

$R_b{}^2$ is H, $C_1$–$C_4$ alkyl, $C_3$–$C_4$ alkenyl or $R_a{}^2$ and $R_b{}^2$ can be taken together to form —$CH_2$—$_5$, —$CH_2$—$_4$ or —$CH_2CH_2$—O—$CH_2CH_2$—;

$R_c{}^2$ is $C_1$–$C_4$ alkyl or $C_3$–$C_4$ alkenyl;

$R^3$ is $C_1$–$C_4$ alkyl or $OCH_3$;

$R^4$ is $C_1$–$C_4$ alkyl;

$R^5$ is $C_1$–$C_3$ alkyl;

X and Z are independently H, $CH_3$, Br, Cl, $OCH_3$, $CH_2CH_3$, $CH_2OCH_3$ or $OCH_2CH_3$; and Y is F, Cl, Br, I, $CH_3$, $CH_2CH_3$, $CH_2CH_2CH_3$, $(CH_2)_3CH_3$, $CH_2$—$CH$=$CH_2$, $OCH_3$, $OCH_2CH_3$, CN, $CH_2CH_2Cl$, $CH_2CH_2CH_2Cl$, $CH_2CH_2OCH_3$, $OCH_2OCH_3$, $CH_2OCH_3$, $OCH_2CH_2OCH_3$, $CH_2CO_2R^6$, $CH_2CH_2CO_2R^6$, $CO_2R^6$,

or NO;

$R^6$ is $CH_3$ or $CH_2CH_3$;

and their agriculturally suitable salts; provided that:
(1) when $R_a{}^2$ is $OCH_3$, then $R_b{}^2$ is $CH_3$;
(2) when $R^3$ is $OCH_3$, then $R^4$ is $CH_3$; and
(3) when R is Cl, then Y is F.

2. A compound of claim 1 wherein R is $CO_2R^2$ or $SO_2NR_3R_4$.

3. A compound of claim 1 wherein $R^1$ is H.

4. A compound of claim 2 wherein $R^1$ is H.

5. A compound of claim 3 wherein $R^2$ is $C_1$—$C_4$ alkyl, $C_3$–$C_4$ alkenyl or $C_2$–$C_3$ haloalkyl, and Y is F, Cl, Br, $CH_3$, $C_2H_5$ or $CH_2CH_2Cl$, and at least one of X or Z is $CH_3$, $OCH_3$, ethyl or ethoxy.

6. A compound of claim 5 wherein X is H, $CH_3$ or $OCH_3$ and Y is F, Cl, Br, $CH_3$, $C_2H_5$ or $CH_2CH_2Cl$.

7. The compound of claim 1, methyl 2-{[(5-chloropyrimidin-2-yl)aminocarbonyl]aminosulfonyl}-benzoate.

8. The compound of claim 1, methyl 2-{[(4-chloro-6-methoxy-5-methylpyrimidin-2-yl)aminocarbonyl]aminosulfonyl}benzoate.

9. The compound of claim 1, methyl 2-[[[4-chloro-5-(2-chloroethyl)-6-methylpyrimidin-2-yl]-aminocarbonyl]aminosulfonyl]benzoate.

10. The compound of claim 1, methyl 2-[[(4,5,6-trimethylpyrimidin-2-yl)aminocarbonyl]aminosulfonyl]benzoate.

11. The compound of claim 1, methyl 2-[[(5-iodo-4,6-dimethylpyrimidin-2-yl)aminocarbonyl]aminosulfonyl]benzoate.

12. The compound of claim 1, methyl 2-[[(5-chloro-4,6-dimethylpyrimidin-2-yl)aminocarbonyl]aminosulfonyl]benzoate.

13. The compound of claim 1, methyl 2-[[(5-bromo-4,6-dimethylpyrimidin-2-yl)aminocarbonyl]aminosulfonyl]benzoate.

14. The compound of claim 1, methyl 2-[[(5-ethyl-4,6-dimethylpyrimidin-2-yl)aminocarbonyl]aminosulfonyl]benzoate.

15. The compound of claim 1, 2-chloro-N-[(5-fluoro-4,6-dimethoxypyrimidin-2-yl)aminocarbonyl]benzenesulfonamide.

16. The compound of claim 1, methyl 2-[[(5-fluoro-4,6-dimethoxypyrimidin-2-yl)aminocarbonyl]aminosulfonyl]benzoate.

17. The compound of claim 1, (2-propenyl 2-[[(5-fluoro-4,6-dimethoxypyrimidin-2-yl)aminocarbonyl]aminosulfonyl]benzoate.

18. The compound of claim 1, methyl 2-[[(5-chloro-4-methylpyrimidin-2-yl)aminocarbonyl]aminosulfonyl]benzoate.

19. The compound of claim 1, methyl 2-[[(5-ethyl-4-methylpyrimidin-2-yl)aminocarbonyl]aminosulfonyl]benzoate.

20. A composition for the control of undesirable vegetation consisting essentially of a compound of claim 1 and at least one of (a) a surface-active agent and (b) a solid or liquid diluent.

21. A composition for the control of undesirable vegetation consisting essentially of a compound of claim 2 and at least one of (a) a surface-active agent and (b) a solid or liquid diluent.

22. A composition for the control of undesirable vegetation consisting essentially of a compound of claim 3 and at least one of (a) a surface-active agent and (b) a solid or liquid diluent.

23. A composition for the control of undesirable vegetation consisting essentially of a compound of claim 4 and at least one of (a) a surface-active agent and (b) a solid or liquid diluent.

24. A composition for the control of undesirable vegetation consisting essentially of a compound of claim 5 and at least one of (a) a surface-active agent and (b) a solid or liquid diluent.

25. A composition for the control of undesirable vegetation consisting essentially of a compound of claim 6 and at least one of (a) a surface-active agent and (b) a solid or liquid diluent.

26. A composition for the control of undesirable vegetation consisting essentially of a compound of claim 7 and at least one of (a) a surface-active agent and (b) a solid or liquid diluent.

27. A composition for the control of undesirable vegetation consisting essentially of a compound of claim 8 and at least one of (a) a surface-active agent and (b) a solid or liquid diluent.

28. A composition for the control of undesirable vegetation consisting essentially of a compound of claim 9 and at least one of (a) a surface-active agent and (b) a solid or liquid diluent.

29. A method for the control of undesirable vegetation comprising applying to the locus of such undesirable vegetation a herbicidally effective amount of a compound of claim 1.

30. A method for the control of undesirable vegetation comprising applying to the locus of such undesirable vegetation a herbicidally effective amount of a compound of claim 2.

31. A method for the control of undesirable vegetation comprising applying to the locus of such undesirable vegetation a herbicidally effective amount of a compound of claim 3.

32. A method for the control of undesirable vegetation comprising applying to the locus of such undesirable vegetation a herbicidally effective amount of a compound of claim 4.

33. A method for the control of undesirable vegetation comprising applying to the locus of such undesirable vegetation a herbicidally effective amount of a compound of claim 5.

34. A method for the control of undesirable vegetation comprising applying to the locus of such undesirable vegetation a herbicidally effective amount of a compound of claim 6.

35. A method for the control of undesirable vegetation comprising applying to the locus of such undesirable vegetation a herbicidally effective amount of a compound of claim 7.

36. A method for the control of undesirable vegetation comprising applying to the locus of such undesirable vegetation a herbicidally effective amount of a compound of claim 8.

37. A method for the control of undesirable vegetation comprising applying to the locus of such undesirable vegetation a herbicidally effective amount of a compound of claim 9.

38. A compound selected from

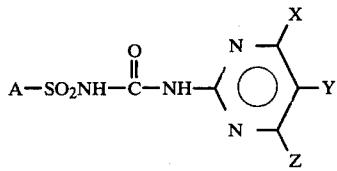  I wherein
A is

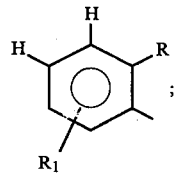 ;

R is $CO_2H$;
$R^1$ is H, Cl, F, Br, $NO_2$, $CH_3$, $OCH_3$ or $CF_3$;
X and Z are independently H, $CH_3$, Br, Cl, $OCH_3$, $CH_2CH_3$, $CH_2OCH_3$ or $OCH_2CH_3$; and
Y is F, Cl, Br, I, $CH_3$, $CH_2CH_3$, $CH_2CH_2CH_3$, $(CH_2)_3CH_3$, $CH_2-CH=CH_2$, $OCH_3$, $OCH_2CH_3$, CN, $CH_2CH_2Cl$, $CH_2CH_2OCH_3$, $OCH_2OCH_3$, $CH_2OCH_3$, $OCH_2CH_2OCH_3$, $$\overset{O}{\underset{\|}{\text{—}}}H$$

or NO;
and their agriculturally suitable salts.

* * * * *